United States Patent
Pecker et al.

(10) Patent No.: US 6,531,129 B2
(45) Date of Patent: Mar. 11, 2003

(54) HEPARANASE SPECIFIC MOLECULAR PROBES AND THEIR USE IN RESEARCH AND MEDICAL APPLICATIONS

(75) Inventors: Iris Pecker, Rishon Le Zion (IL); Israel Vlodavsky, Mevaseret Zion (IL); Yael Friedman, Jerusalem (IL); Tuvia Perets, Ramat Gan (IL)

(73) Assignees: Insight Strategy & Marketing Ltd., Rehovot (IL); Hadasit Medical Research Services and Development Ltd., Jerusalem (IL)

( * ) Notice: Subject to any disclaimer, the term of this patent is extended or adjusted under 35 U.S.C. 154(b) by 0 days.

(21) Appl. No.: 09/322,977

(22) Filed: Jun. 1, 1999

(65) Prior Publication Data

US 2002/0114801 A1 Aug. 22, 2002

Related U.S. Application Data

(60) Division of application No. 09/071,739, filed on May 1, 1998, now Pat. No. 6,177,545, which is a continuation-in-part of application No. 08/922,170, filed on Sep. 2, 1997, now Pat. No. 5,968,822.

(51) Int. Cl.[7] ............................................. A61K 39/395
(52) U.S. Cl. ............................... 424/139.1; 424/130.1; 424/146.1; 435/7.1
(58) Field of Search ........................... 424/146.1, 130.1, 424/139.1; 435/7.1

(56) References Cited

U.S. PATENT DOCUMENTS 5,332,812 A * 7/1994 Nicolson et al.

FOREIGN PATENT DOCUMENTS

WO        WO 88/01280        * 2/1988

OTHER PUBLICATIONS

Mollinedo et al. Biochem J. vol. 327, pp. 917–923, 1997.*
Harlow et al. Antibodies A Laboratory Manual. Eds. Harlow et al., pp. 471–510, 1988.*
Kosir et al. J. Surg. Res. 67: 98–105, Jan. 1997.*
Marchetti et al. Cancer Res. 56: 2856–2863, Jun. 1996.*
Nakajima et al. (J. Cell Biochemistry 1988; 36: 157–167).*
Bost et al. (Immunol. Invest. 1988; 17:577–586).*
Bendayan (J. Histochem. Cytochem. 1995; 43: 881–886).*
Coleman et al. (Research in Immunology, 1994; 145(1): 33–36).*
Abaza et al. (Journal of Protein Chemistry, vol. 11, No. 5, 1992, pp. 433–444.*
Lederman et al. (Molecular Immunology 28: 1171–1181, 1991).*
Li et al. (PNAS 77: 3211–3214, 1980).*
Ngo et al.; in The Protein Folding Problem and Tertiary Structure Prediction,1994, Merz et al., (ed.), Birkhauser, Boston, MA, pp. 433 and 492–495.*

* cited by examiner

Primary Examiner—Patrick J. Nolan
Assistant Examiner—Amy DeCloux
(74) Attorney, Agent, or Firm—G. E. Ehrlich LTD

(57) ABSTRACT

A variety of heparanase specific molecular probes which can be used for research and medical applications including diagnosis and therapy are disclosed. Specific applications include the use of a heparanase specific molecular probe for detection of the presence, absence or level of heparanase expression; the use of a heparanase specific molecular probe for therapy of a condition associated with expression of heparanase; the use of a heparanase specific molecular probe for quantification of heparanase in a body fluid; the use of a heparanase specific molecular probe for targeted drug delivery; and, the use of a heparanase specific molecular probe as a therapeutic agent.

6 Claims, 18 Drawing Sheets

(7 of 18 Drawing Sheet(s) Filed in Color)

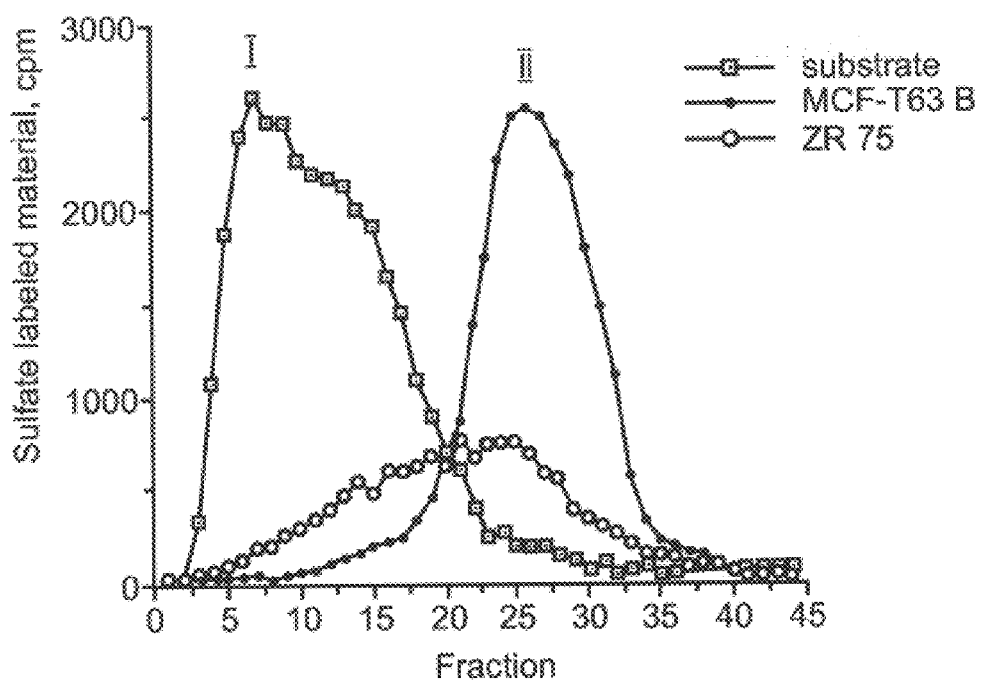
Fig. 2b
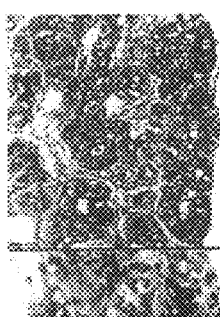Fig. 3a 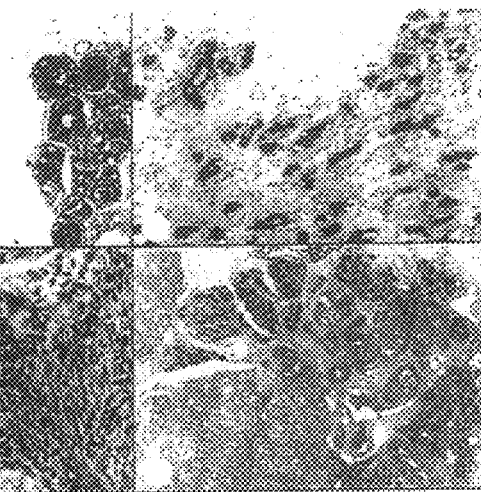Fig. 3b
Fig. 3c 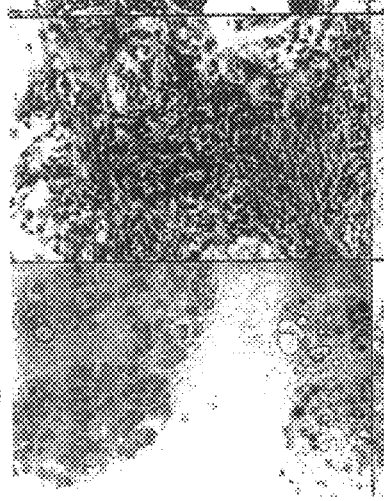Fig. 3d
Fig. 3e 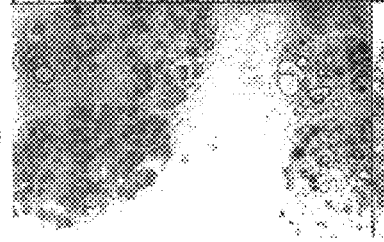 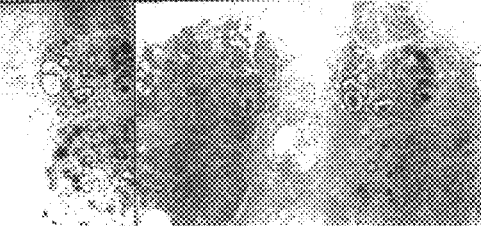Fig. 3f

Fig. 9c
Fig. 9d
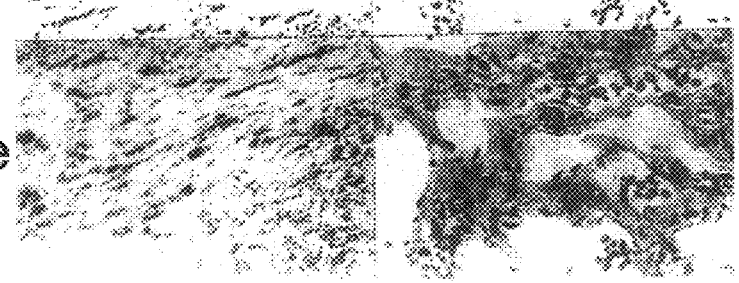
Fig. 9e
Fig. 9f

Fig. 10d

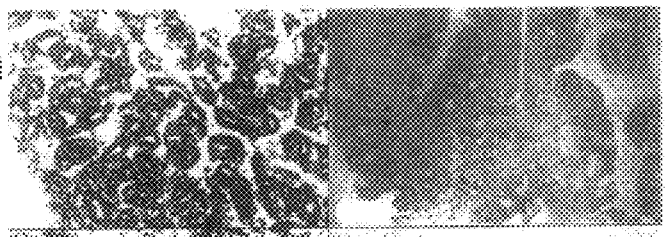
Fig. 11a  Fig. 11b
Fig. 11c  Fig. 11d
Fig. 11e  Fig. 11f
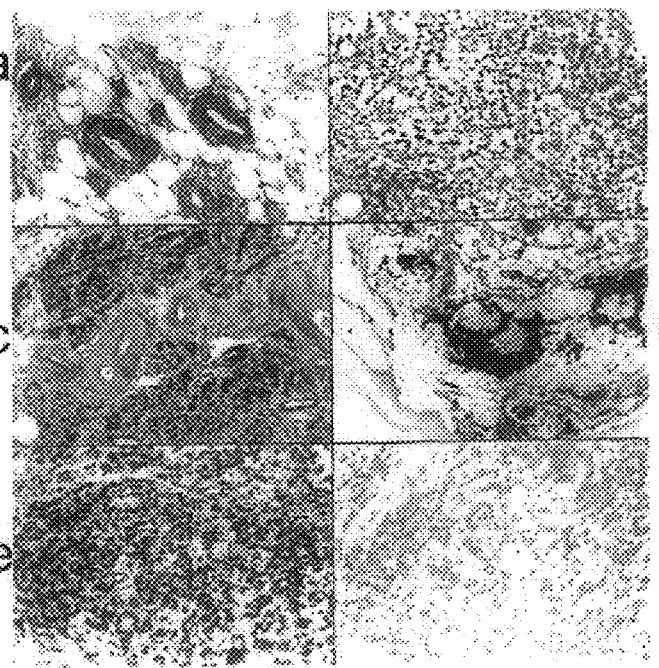
Fig. 12a  Fig. 12b
Fig. 12c  Fig. 12d
Fig. 12e  Fig. 12f

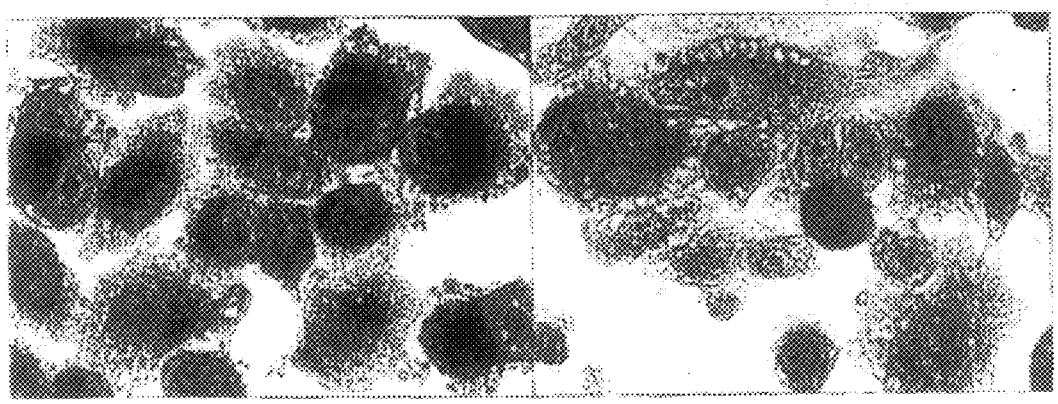
Fig. 22a    Fig. 22b
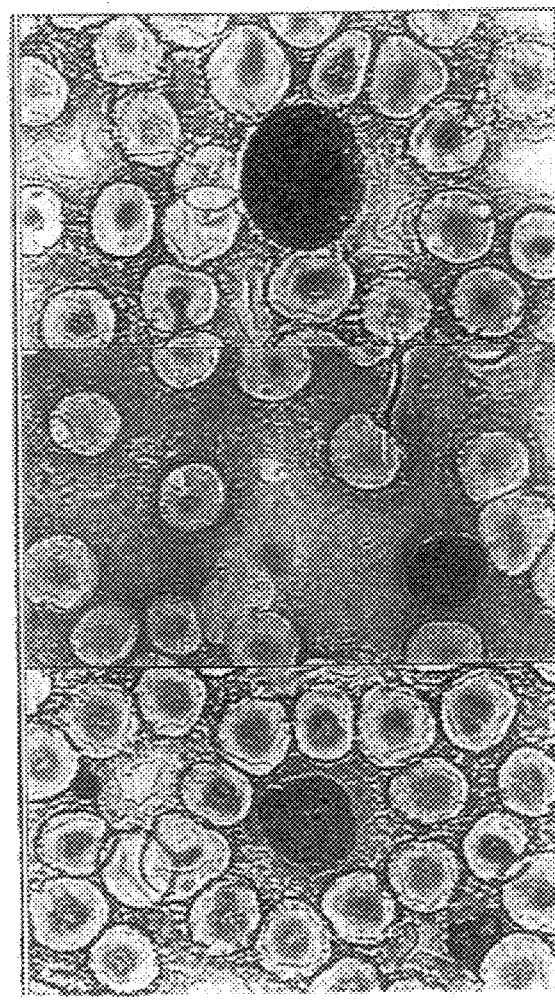
Fig. 23a
Fig. 23b
Fig. 23c

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH:1721
        (B) TYPE:nucleic acid
        (C) STRANDEDNESS:double
        (D) TOPOLOGY:linear (xi) SEQUENCE DESCRIPTION: SEQ ID NO:1:

```
CTAGAGCTTT CGACTCTCCG CTGCGCGGCA GCTGGCGGGG GGAGCAGCCA GGTGAGCCCA          60

AGATGCTGCT GCGCTCGAAG CCTGCGCTGC CGCCGCCGCT GATGCTGCTG CTCCTGGGGC         120

CGCTGGGTCC CCTCTCCCCT GGCGCCCTGC CCCGACCTGC GCAAGCACAG GACGTCGTGG         180

ACCTGGACTT cTTCACCCAG GAGCCGCTGC ACCTGGTGAG CCCCTCGTTC CTGTCCGTCA         240

CCATTGACGC CAACCTGGCC ACGGACCCGC GGTTCCTCAT CCTCCTGGGT TCTCCAAAGC         300

TTCGTACCTT GGCCAGAGGC TTGTCTCCTG CGTACCTGAG GTTTGGTGGC ACCAAGACAG         360

ACTTCCTAAT TTTCGATCCC AAGAAGGAAT CAACCTTTGA AGAGAGAAGT TACTGGCAAT         420

CTCAAGTCAA CCAGGATATT TGCAAATATG GATCCATCCC TCCTGATGTG GAGGAGAAGT         480

TACGGTTGGA ATGGCCCTAC CAGGAGCAAT TGCTACTCCG AGAACACTAC CAGAAAAAGT         540

TCAAGAACAG CACCTACTCA AGAAGCTCTG TAGATGTGCT ATACACTTTT GCAAACTGCT         600

CAGGACTGGA CTTGATCTTT GGCCTAAATG CGTTATTAAG AACAGCAGAT TTGCAGTGGA         660

ACAGTTCTAA TGCTCAGTTG CTCCTGGACT ACTGCTCTTC CAAGGGGTAT AACATTTCTT         720

GGGAACTAGG CAATGAACCT AACAGTTTCC TTAAGAAGGC TGATATTTTC ATCAATGGGT         780

CGCAGTTAGG AGAAGATTAT ATTCAATTGC ATAAACTTCT AAGAAAGTCC ACCTTCAAAA         840

ATGCAAAACT CTATGGTCCT GATGTTGGTC AGCCTCGAAG AAAGACGGCT AAGATGCTGA         900

AGAGCTTCCT GAAGGCTGGT GGAGAAGTGA TTGATTCAGT TACATGGCAT CACTACTATT         960

TGAATGGACG GACTGCTACC AGGGAAGATT TTCTAAACCC TGATGTATTG GACATTTTTA        1020

TTTCATCTGT GCAAAAAGTT TTCCAGGTGG TTGAGAGCAC CAGGCCTGGC AAGAAGGTCT        1080

GGTTAGGAGA AACAAGCTCT GCATATGGAG GCGGAGCGCC CTTGCTATCC GACACCTTTG        1140

CAGCTGGCTT TATGTGGCTG GATAAATTGG GCCTGTCAGC CCGAATGGGA ATAGAAGTGG        1200

TGATGAGGCA AGTATTCTTT GGAGCAGGAA ACTACCATTT AGTGGATGAA AACTTCGATC        1260

CTTTACCTGA TTATTGGCTA TCTCTTCTGT TCAAGAAATT GGTGGGCACC AAGGTGTTAA        1320

TGGCAAGCGT GCAAGGTTCA AAGAGAAGGA AGCTTCGAGT ATACCTTCAT TGCACAAACA        1380

CTGACAATCC AAGGTATAAA GAAGGAGATT TAACTCTGTA TGCCATAAAC CTCCATAACG        1440

TCACCAAGTA CTTGCGGTTA CCCTATCCTT TTTCTAACAA GCAAGTGGAT AAATACCTTC        1500

TAAGACCTTT GGGACCTCAT GGATTACTTT CCAAATCTGT CCAACTCAAT GGTCTAACTC        1560
```

```
TAAAGATGGT GGATGATCAA ACCTTGCCAC CTTTAATGGA AAAACCTCTC CGGCCAGGAA    1620

GTTCACTGGG CTTGCCAGCT TTCTCATATA GTTTTTTTGT GATAAGAAAT GCCAAAGTTG    1680

CTGCTTGCAT CTGAAAATAA AATATACTAG TCCTGACACT G                        1721
```

(2) INFORMATION FOR SEQ ID NO:2:

(i) SEQUENCE CHARACTERISTICS:
        (A) LENGTH:543
        (B) TYPE:amino acid
        (C) STRANDEDNESS:single
        (D) TOPOLOGY:linear (xi) SEQUENCE DESCRIPTION: SEQ ID NO:2:

```
Met Leu Leu Arg Ser Lys Pro Ala Leu Pro Pro Leu Met Leu Leu
                 5                  10                  15

Leu Leu Gly Pro Leu Gly Pro Leu Ser Pro Gly Ala Leu Pro Arg Pro
             20                  25                  30

Ala Gln Ala Gln Asp Val Val Asp Leu Asp Phe Phe Thr Gln Glu Pro
         35                  40                  45

Leu His Leu Val Ser Pro Ser Phe Leu Ser Val Thr Ile Asp Ala Asn
     50                  55                  60

Leu Ala Thr Asp Pro Arg Phe Leu Ile Leu Leu Gly Ser Pro Lys Leu
 65                  70                  75                  80

Arg Thr Leu Ala Arg Gly Leu Ser Pro Ala Tyr Leu Arg Phe Gly Gly
                 85                  90                  95

Thr Lys Thr Asp Phe Leu Ile Phe Asp Pro Lys Lys Glu Ser Thr Phe
            100                 105                 110

Glu Glu Arg Ser Tyr Trp Gln Ser Gln Val Asn Gln Asp Ile Cys Lys
        115                 120                 125

Tyr Gly Ser Ile Pro Pro Asp Val Glu Glu Lys Leu Arg Leu Glu Trp
    130                 135                 140

Pro Tyr Gln Glu Gln Leu Leu Leu Arg Glu His Tyr Gln Lys Lys Phe
145                 150                 155                 160

Lys Asn Ser Thr Tyr Ser Arg Ser Ser Val Asp Val Leu Tyr Thr Phe
                165                 170                 175

Ala Asn Cys Ser Gly Leu Asp Leu Ile Phe Gly Leu Asn Ala Leu Leu
            180                 185                 190

Arg Thr Ala Asp Leu Gln Trp Asn Ser Ser Asn Ala Gln Leu Leu Leu
        195                 200                 205

Asp Tyr Cys Ser Ser Lys Gly Tyr Asn Ile Ser Trp Glu Leu Gly Asn
    210                 215                 220

Glu Pro Asn Ser Phe Leu Lys Lys Ala Asp Ile Phe Ile Asn Gly Ser
225                 230                 235                 240

Gln Leu Gly Glu Asp Tyr Ile Gln Leu His Lys Leu Leu Arg Lys Ser
                245                 250                 255

Thr Phe Lys Asn Ala Lys Leu Tyr Gly Pro Asp Val Gly Gln Pro Arg
            260                 265                 270

Arg Lys Thr Ala Lys Met Leu Lys Ser Phe Leu Lys Ala Gly Gly Glu
        275                 280                 285

Val Ile Asp Ser Val Thr Trp His His Tyr Tyr Leu Asn Gly Arg Thr
    290                 295                 300

Ala Thr Arg Glu Asp Phe Leu Asn Pro Asp Val Leu Asp Ile Phe Ile
305                 310                 315                 320

Ser Ser Val Gln Lys Val Phe Gln Val Val Glu Ser Thr Arg Pro Gly
```

```
                        325                 330                 335
Lys Lys Val Trp Leu Gly Glu Thr Ser Ser Ala Tyr Gly Gly Gly Ala
                340                 345                 350

Pro Leu Leu Ser Asp Thr Phe Ala Ala Gly Phe Met Trp Leu Asp Lys
                355                 360                 365

Leu Gly Leu Ser Ala Arg Met Gly Ile Glu Val Val Met Arg Gln Val
    370                 375                 380

Phe Phe Gly Ala Gly Asn Tyr His Leu Val Asp Glu Asn Phe Asp Pro
385                 390                 395                 400

Leu Pro Asp Tyr Trp Leu Ser Leu Leu Phe Lys Lys Leu Val Gly Thr
                405                 410                 415

Lys Val Leu Met Ala Ser Val Gln Gly Ser Lys Arg Arg Lys Leu Arg
                420                 425                 430

Val Tyr Leu His Cys Thr Asn Thr Asp Asn Pro Arg Tyr Lys Glu Gly
                435                 440                 445

Asp Leu Thr Leu Tyr Ala Ile Asn Leu His Asn Val Thr Lys Tyr Leu
    450                 455                 460

Arg Leu Pro Tyr Pro Phe Ser Asn Lys Gln Val Asp Lys Tyr Leu Leu
465                 470                 475                 480

Arg Pro Leu Gly Pro His Gly Leu Leu Ser Lys Ser Val Gln Leu Asn
                485                 490                 495

Gly Leu Thr Leu Lys Met Val Asp Asp Gln Thr Leu Pro Pro Leu Met
                500                 505                 510

Glu Lys Pro Leu Arg Pro Gly Ser Ser Leu Gly Leu Pro Ala Phe Ser
                515                 520                 525

Tyr Ser Phe Phe Val Ile Arg Asn Ala Lys Val Ala Ala Cys Ile
                530                 535                 540     543

(2) INFORMATION FOR SEQ ID NO:3:

(i) SEQUENCE CHARACTERISTICS:
        (A) LENGTH:1721
        (B) TYPE:Nucleic acid
        (C) STRANDEDNESS:Double
        (D) TOPOLOGY:linear (xi) SEQUENCE DESCRIPTION: SEQ ID NO:3:

CT AGA GCT TTC GAC      14

TCT CCG CTG CGC GGC AGC TGG CGG GGG GAG CAG CCA GGT GAG CCC AAG       62

ATG CTG CTG CGC TCG AAG CCT GCG CTG CCG CCG CCG CTG ATG CTG CTG      110
Met Leu Leu Arg Ser Lys Pro Ala Leu Pro Pro Pro Leu Met Leu Leu
                5                  10                  15

CTC CTG GGG CCG CTG GGT CCC CTC TCC CCT GGC GCC CTG CCC CGA CCT      158
Leu Leu Gly Pro Leu Gly Pro Leu Ser Pro Gly Ala Leu Pro Arg Pro
            20                  25                  30

GCG CAA GCA CAG GAC GTC GTG GAC CTG GAC TTC TTC ACC CAG GAG CCG      206
Ala Gln Ala Gln Asp Val Val Asp Leu Asp Phe Phe Thr Gln Glu Pro
        35                  40                  45

CTG CAC CTG GTG AGC CCC TCG TTC CTG TCC GTC ACC ATT GAC GCC AAC      254
Leu His Leu Val Ser Pro Ser Phe Leu Ser Val Thr Ile Asp Ala Asn
    50                  55                  60

CTG GCC ACG GAC CCG CGG TTC CTC ATC CTC CTG GGT TCT CCA AAG CTT      302
Leu Ala Thr Asp Pro Arg Phe Leu Ile Leu Leu Gly Ser Pro Lys Leu
65                  70                  75                  80

CGT ACC TTG GCC AGA GGC TTG TCT CCT GCG TAC CTG AGG TTT GGT GGC      350
Arg Thr Leu Ala Arg Gly Leu Ser Pro Ala Tyr Leu Arg Phe Gly Gly
                85                  90                  95
```

```
ACC AAG ACA GAC TTC CTA ATT TTC GAT CCC AAG AAG GAA TCA ACC TTT        398
Thr Lys Thr Asp Phe Leu Ile Phe Asp Pro Lys Lys Glu Ser Thr Phe
            100                 105                 110

GAA GAG AGA AGT TAC TGG CAA TCT CAA GTC AAC CAG GAT ATT TGC AAA        446
Glu Glu Arg Ser Tyr Trp Gln Ser Gln Val Asn Gln Asp Ile Cys Lys
            115                 120                 125

TAT GGA TCC ATC CCT CCT GAT GTG GAG GAG AAG TTA CGG TTG GAA TGG        494
Tyr Gly Ser Ile Pro Pro Asp Val Glu Glu Lys Leu Arg Leu Glu Trp
130                 135                 140

CCC TAC CAG GAG CAA TTG CTA CTC CGA GAA CAC TAC CAG AAA AAG TTC        542
Pro Tyr Gln Glu Gln Leu Leu Leu Arg Glu His Tyr Gln Lys Lys Phe
145                 150                 155                 160

AAG AAC AGC ACC TAC TCA AGA AGC TCT GTA GAT GTG CTA TAC ACT TTT        590
Lys Asn Ser Thr Tyr Ser Arg Ser Ser Val Asp Val Leu Tyr Thr Phe
            165                 170                 175

GCA AAC TGC TCA GGA CTG GAC TTG ATC TTT GGC CTA AAT GCG TTA TTA        638
Ala Asn Cys Ser Gly Leu Asp Leu Ile Phe Gly Leu Asn Ala Leu Leu
            180                 185                 190

AGA ACA GCA GAT TTG CAG TGG AAC AGT TCT AAT GCT CAG TTG CTC CTG        686
Arg Thr Ala Asp Leu Gln Trp Asn Ser Ser Asn Ala Gln Leu Leu Leu
            195                 200                 205

GAC TAC TGC TCT TCC AAG GGG TAT AAC ATT TCT TGG GAA CTA GGC AAT        734
Asp Tyr Cys Ser Ser Lys Gly Tyr Asn Ile Ser Trp Glu Leu Gly Asn
210                 215                 220

GAA CCT AAC AGT TTC CTT AAG AAG GCT GAT ATT TTC ATC AAT GGG TCG        782
Glu Pro Asn Ser Phe Leu Lys Lys Ala Asp Ile Phe Ile Asn Gly Ser
225                 230                 235                 240

CAG TTA GGA GAA GAT TAT ATT CAA TTG CAT AAA CTT CTA AGA AAG TCC        830
Gln Leu Gly Glu Asp Tyr Ile Gln Leu His Lys Leu Leu Arg Lys Ser
            245                 250                 255

ACC TTC AAA AAT GCA AAA CTC TAT GGT CCT GAT GTT GGT CAG CCT CGA        878
Thr Phe Lys Asn Ala Lys Leu Tyr Gly Pro Asp Val Gly Gln Pro Arg
            260                 265                 270

AGA AAG ACG GCT AAG ATG CTG AAG AGC TTC CTG AAG GCT GGT GGA GAA        926
Arg Lys Thr Ala Lys Met Leu Lys Ser Phe Leu Lys Ala Gly Gly Glu
            275                 280                 285

GTG ATT GAT TCA GTT ACA TGG CAT CAC TAC TAT TTG AAT GGA CGG ACT        974
Val Ile Asp Ser Val Thr Trp His His Tyr Tyr Leu Asn Gly Arg Thr
290                 295                 300

GCT ACC AGG GAA GAT TTT CTA AAC CCT GAT GTA TTG GAC ATT TTT ATT       1022
Ala Thr Arg Glu Asp Phe Leu Asn Pro Asp Val Leu Asp Ile Phe Ile
305                 310                 315                 320

TCA TCT GTG CAA AAA GTT TTC CAG GTG GTT GAG AGC ACC AGG CCT GGC       1070
Ser Ser Val Gln Lys Val Phe Gln Val Val Glu Ser Thr Arg Pro Gly
            325                 330                 335

AAG AAG GTC TGG TTA GGA GAA ACA AGC TCT GCA TAT GGA GGC GGA GCG       1118
Lys Lys Val Trp Leu Gly Glu Thr Ser Ser Ala Tyr Gly Gly Gly Ala
            340                 345                 350

CCC TTG CTA TCC GAC ACC TTT GCA GCT GGC TTT ATG TGG CTG GAT AAA       1166
Pro Leu Leu Ser Asp Thr Phe Ala Ala Gly Phe Met Trp Leu Asp Lys
            355                 360                 365

TTG GGC CTG TCA GCC CGA ATG GGA ATA GAA GTG GTG ATG AGG CAA GTA       1214
Leu Gly Leu Ser Ala Arg Met Gly Ile Glu Val Val Met Arg Gln Val
370                 375                 380

TTC TTT GGA GCA GGA AAC TAC CAT TTA GTG GAT GAA AAC TTC GAT CCT       1262
Phe Phe Gly Ala Gly Asn Tyr His Leu Val Asp Glu Asn Phe Asp Pro
385                 390                 395                 400

TTA CCT GAT TAT TGG CTA TCT CTT CTG TTC AAG AAA TTG GTG GGC ACC       1310
Leu Pro Asp Tyr Trp Leu Ser Leu Leu Phe Lys Lys Leu Val Gly Thr
```

|     |     |     |     |     |     | 405 |     |     |     | 410 |     |     |     |     | 415 |     |      |
|---|---|---|---|---|---|---|---|---|---|---|---|---|---|---|---|---|---|

```
AAG GTG TTA ATG GCA AGC GTG CAA GGT TCA AAG AGA AGG AAG CTT CGA      1358
Lys Val Leu Met Ala Ser Val Gln Gly Ser Lys Arg Arg Lys Leu Arg
            420                 425                 430

GTA TAC CTT CAT TGC ACA AAC ACT GAC AAT CCA AGG TAT AAA GAA GGA      1406
Val Tyr Leu His Cys Thr Asn Thr Asp Asn Pro Arg Tyr Lys Glu Gly
                435                 440                 445

GAT TTA ACT CTG TAT GCC ATA AAC CTC CAT AAC GTC ACC AAG TAC TTG      1454
Asp Leu Thr Leu Tyr Ala Ile Asn Leu His Asn Val Thr Lys Tyr Leu
        450                 455                 460

CGG TTA CCC TAT CCT TTT TCT AAC AAG CAA GTG GAT AAA TAC CTT CTA      1502
Arg Leu Pro Tyr Pro Phe Ser Asn Lys Gln Val Asp Lys Tyr Leu Leu
465                 470                 475                 480

AGA CCT TTG GGA CCT CAT GGA TTA CTT TCC AAA TCT GTC CAA CTC AAT      1550
Arg Pro Leu Gly Pro His Gly Leu Leu Ser Lys Ser Val Gln Leu Asn
                485                 490                 495

GGT CTA ACT CTA AAG ATG GTG GAT GAT CAA ACC TTG CCA CCT TTA ATG      1598
Gly Leu Thr Leu Lys Met Val Asp Asp Gln Thr Leu Pro Pro Leu Met
        500                 505                 510

GAA AAA CCT CTC CGG CCA GGA AGT TCA CTG GGC TTG CCA GCT TTC TCA      1646
Glu Lys Pro Leu Arg Pro Gly Ser Ser Leu Gly Leu Pro Ala Phe Ser
    515                 520                 525

TAT AGT TTT TTT GTG ATA AGA AAT GCC AAA GTT GCT GCT TGC ATC TGA      1694
Tyr Ser Phe Phe Val Ile Arg Asn Ala Lys Val Ala Ala Cys Ile
530                 535                 540         543

AAA TAA AAT ATA CTA GTC CTG ACA CTG                                  1721
```

(2) INFORMATION FOR SEQ ID NO:4:

(i) SEQUENCE CHARACTERISTICS:
        (A) LENGTH:26
        (B) TYPE:nucleic acid
        (C) STRANDEDNESS:single
        (D) TOPOLOGY:linear (xi) SEQUENCE DESCRIPTION: SEQ ID NO:4:

CGCATATGCA GGACGTCGTG GACCTG                                                   26

(2) INFORMATION FOR SEQ ID NO:5:

(i) SEQUENCE CHARACTERISTICS:
        (A) LENGTH:24
        (B) TYPE:nucleic acid
        (C) STRANDEDNESS:single
        (D) TOPOLOGY:linear (xi) SEQUENCE DESCRIPTION: SEQ ID NO:5:

TATGATCCTC TAGTACTTCT CGAC                                                     24

(2) INFORMATION FOR SEQ ID NO:6:

(i) SEQUENCE CHARACTERISTICS:
        (A) LENGTH:23
        (B) TYPE:nucleic acid
        (C) STRANDEDNESS:single
        (D) TOPOLOGY:linear (xi) SEQUENCE DESCRIPTION: SEQ ID NO:6:

TTCGATCCCA AGAAGGAATC AAC                                                      23

(2) INFORMATION FOR SEQ ID NO:7:

(i) SEQUENCE CHARACTERISTICS:

```
        (A) LENGTH:24
        (B) TYPE:nucleic acid
        (C) STRANDEDNESS:single
        (D) TOPOLOGY:linear (xi) SEQUENCE DESCRIPTION: SEQ ID NO:7:

GTAGTGATGC CATGTAACTG AATC                                              24
```

HEPARANASE SPECIFIC MOLECULAR PROBES AND THEIR USE IN RESEARCH AND MEDICAL APPLICATIONS

This is a divisional of U.S. patent application Ser. No. 09/071,739, filed May 1, 1998, U.S. Pat. No. 6,177,545, which is a continuation-in-part of U.S. patent application Ser. No. 08/922,170, filed Sep. 2, 1997, U.S. Pat. No. 5,968,822.

FIELD AND BACKGROUND OF THE INVENTION

The present invention relates to heparanase specific molecular probes their use in research and medical applications. More particularly, the present invention relates to the use of heparanase specific molecular probes, such as anti-heparanase antibodies (both poly- and monoclonal) and heparanase gene (hpa) derived nucleic acids, including, but not limited to, PCR primers, antisense oligonucleotide probes, antisense RNA probes, DNA probes and the like for detection and monitoring of malignancies, metastasis and other non-malignant conditions, efficiency of therapeutic treatments, targeted drug delivery and therapy.

Heparan Sulfate Proteoglycans (HSPGs):

HSPGs are ubiquitous macromolecules associated with the cell surface and extracellular matrix (ECM) of a wide range of cells of vertebrate and invertebrate tissues (1–5). The basic HSPG structure consists of a protein core to which several linear heparan sulfate chains are covalently attached. The polysaccharide chains are typically composed of repeating hexuronic and D-glucosamine disaccharide units that are substituted to a varying extent with N- and O-linked sulfate moieties and N-linked acetyl groups (1–5). Studies on the involvement of ECM molecules in cell attachment, growth and differentiation revealed a central role of HSPGs in embryonic morphogenesis, angiogenesis, metastasis, neurite outgrowth and tissue repair (1–5). The heparan sulfate (HS) chains, unique in their ability to bind a multitude of proteins, ensure that a wide variety of effector molecules cling to the cell surface (4–6). HSPGs are also prominent components of blood vessels (3). In large vessels they are concentrated mostly in the intima and inner media, whereas in capillaries they are found mainly in the subendothelial basement membrane where they support proliferating and migrating endothelial cells and stabilize the structure of the capillary wall. The ability of HSPGs to interact with ECM macromolecules such as collagen, laminin and fibronectin, and with different attachment sites on plasma membranes suggests a key role for this proteoglycan in the self-assembly and insolubility of ECM components, as well as in cell adhesion and locomotion. Cleavage of HS may therefore result in disassembly of the subendothelial ECM and hence may play a decisive role in extravasation of blood-borne cells (7–9). HS catabolism is observed in inflammation, wound repair, diabetes, and cancer metastasis, suggesting that enzymes which degrade HS play important roles in pathologic processes.

Involvement of Heparanase in Tumor Cell Invasion and Metastasis:

Circulating tumor cells arrested in the capillary beds of different organs must invade the endothelial cell lining and degrade its underlying basement membrane (BM) in order to escape into the extravascular tissue(s) where they establish metastasis (10). Several cellular enzymes (e.g., collagenase IV, plasminogen activator, cathepsin B, elastase) are thought to be involved in degradation of the BM (10). Among these enzymes is an endo-β-D-glucuronidase (heparanase) that cleaves HS at specific intrachain sites (7, 9, 11–12). Expression of a HS degrading heparanase was found to correlate with the metastatic potential of mouse lymphoma (11), fibrosarcoma and melanoma (9) cells. Treatment of experimental animals with heparanase inhibitors (i.e. non-anticoagulant species of low MW heparin) markedly reduced (>90%) the incidence of lung metastases induced by B16 melanoma, Lewis lung carcinoma and mammary adenocarcinoma cells (8, 9, 13).

Heparanase activity could not be detected in normal stromal fibroblasts, mesothelial, endothelial and smooth muscle cells derived from non cancerous biopsies and effusions (12). These observations indicate that heparanase expression may serve as a marker for tumor cells and in particular for those which are highly invasive or potentially invasive. If the same conclusion can be reached by immunostaining of tissue specimens, anti-heparanase antibodies may be applied for early detection and diagnosis of metastatic cell populations and micro-metastases.

Our studies on the control of tumor progression by its local environment, focus on the interaction of cells with the extracellular matrix (ECM) produced by cultured corneal and vascular endothelial cells (EC) (14, 15). This ECM closely resembles the subendothelium in vivo in its morphological appearance and molecular composition. It contains collagens (mostly type III and IV, with smaller amounts of types I and V), proteoglycans (mostly heparan sulfate- and dermatan sulfate- proteoglycans, with smaller amounts of chondroitin sulfate proteoglycans), laminin, fibronectin, entactin and elastin (13, 14). The ability of cells to degrade HS in the ECM was studied by allowing cells to interact with a metabolically sulfate labeled ECM, followed by gel filtration (Sepharose 6B) analysis of degradation products released into the culture medium (11). While intact HSPG are eluted next to the void volume of the column (Kav<0.2, Mr~$0.5 \times 10^6$), labeled degradation fragments of HS side chains are eluted more toward the Vt of the column (0.5<kav<0.8, Mr=$5-7 \times 10^3$) (11).

Possible Involvement of Heparanase in Tumor Angiogenesis:

Fibroblast growth factors are a family of structurally related polypeptides characterized by high affinity to heparin (16). They are highly mitogenic for vascular endothelial cells (EC) and are among the most potent inducers of neovascularization (16, 17). Basic fibroblast growth factor (bFGF) has been extracted from subendothelial ECM produced in vitro and from BM of the cornea, suggesting that ECM may serve as a reservoir for bFGF (18). Studies on the interaction of bFGF with ECM revealed that bFGF binds to HSPG in the ECM and can be released in an active form by HS degrading enzymes (19, 20). Heparanase activity expressed by platelets, mast cells, neutrophils, and lymphoma cells releases active bFGF from ECM and BM (20), suggesting that heparanase may not only function in cell migration and invasion, but may also elicit an indirect neovascular response (18). These results suggest that the ECM HSPGs provide a natural storage depot for bFGF and possibly other heparin-binding growth promoting factors. Displacement of bFGF from its storage within ECM may therefore provide a novel mechanism for induction of neovascularization in normal and pathological situations (6, 18).

Expression of Heparanase by Cells of the Immune System:

Heparanase activity correlates with the ability of activated cells of the immune system to leave the circulation and elicit both inflammatory and autoimmune responses. Interaction of platelets, granulocytes, T and B lymphocytes, macrophages and mast cells with the subendothelial ECM is associated with degradation of heparan sulfate (HS) by heparanase activity (7). The enzyme is released from intracellular compartments (e.g., lysosomes, specific granules) in response to various activation signals (e.g., thrombin, calcium ionophore, immune complexes, antigens, mitogens), suggesting its regulated involvement and presence in inflammatory sites and autoimmune lesions. Heparan sulfate degrading enzymes released by platelets and macrophages are likely to be present in atherosclerotic lesions (21). Hence, cDNA probes and anti-heparanase antibodies may be applied for detection and early diagnosis of these lesions.

Cloning and Expression of the Heparanase Gene:

The cloning and expression of the human heparanase gene are described in U.S. patent application Ser. No. 08/922,170, which is incorporated by reference as if fully set forth herein. A purified fraction of heparanase isolated from human hepatoma cells was subjected to tryptic digestion. Peptides were separated by high pressure liquid chromatography and micro sequenced. The sequence of one of the peptides was used to screen data bases for homology to the corresponding back translated DNA sequence. This procedure led to the identification of a clone containing an insert of 1020 base pairs (bp) which included an open reading frame of 963 bp followed by 27 bp of 3' untranslated region and a Poly A tail. The new gene was designated hpa. Cloning of the missing 5' end of hpa cDNA was performed by PCR amplification of DNA from placenta cDNA composite. The plasmid containing the entire heparanase cDNA was designated phpa. The joined cDNA fragment contained an open reading frame which encodes a polypeptide of 543 amino acids with a calculated molecular weight (MW) of 61,192 daltons. The ability of the hpa gene product to catalyze degradation of heparan sulfate (HS) in vitro was examined by expressing the entire open reading frame of hpa in High five and Sf21 insect cells, using the Baculovirus expression system. Extracts of infected cells were assayed for heparanase activity. For this purpose, cell lysates were incubated with sulfate labeled, ECM-derived HSPG (peak I), followed by gel filtration analysis (Sepharose 6B) of the reaction mixture. While the substrate alone consisted of high molecular weight (MW) material, incubation of the HSPG substrate with lysates of cells infected with hpa containing virus resulted in a complete conversion of the high MW substrate into low MW labeled heparan sulfate degradation fragments.

In subsequent experiments, the labeled HSPG substrate was incubated with the culture medium of infected High Five and Sf21 cells. Heparanase activity, reflected by the conversion of the high MW HSPG substrate into low MW HS degradation fragments, was found in the culture medium of cells infected with the pFhpa virus, but not the control pF1 virus. Altogether, these results indicate that the heparanase enzyme is expressed in an active form by cells infected with Baculovirus containing the newly identified human hpa gene. In other experiments, we have demonstrated that the heparanase enzyme expressed by cells infected with the pFhpa virus is capable of degrading HS complexed to other macromolecular constituents (e.g., fibronectin, laminin, collagen) present in a naturally produced intact ECM, in a manner similar to that reported for highly metastatic tumor cells or activated cells of the immune system.

Purification of the Recombinant Heparanase Enzyme:

The purification of the human heparanase gene are described in U.S. patent application Ser. No. 08/922,170, which is incorporated by reference as if fully set forth herein. Sf21 insect cells were infected with pFhpa virus and the culture medium was applied onto a heparin-Sepharose column. Fractions were eluted with a salt gradient (0.35–2 M NaCl) and tested for heparanase activity and protein profile (SDS/PAGE followed by silver staining). Heparanase activity correlated with the appearance of a protein band of about 63 kDa in fractions 19–24, consistent with the expected MW of the hpa gene product. Active fractions eluted from heparin-Sepharose were pooled, concentrated and applied onto a Superdex 75 FPLC gel filtration column. Aliquots of each fraction were tested for heparanase activity and protein profile. A correlation was found between the appearance of a major protein of about 63 kDa in fractions 4–7 and heparanase activity. This protein was not present in medium conditioned by control non-infected Sf21 cells and subjected to the same purification protocol.

Research on the involvement of heparanase/HS in tumor cell metastasis and angiogenesis has been handicapped by the lack of biological tools (i.e., molecular probes, antibodies) to explore a causative role of heparanase in disease. U.S. patent application Ser. No. 08/922,170 offers, for the first time, a good opportunity to elucidate the enzyme's involvement in tumor metastasis and angiogenesis and the related diagnostic applications.

On the basis of the examples described below, it appears that cDNA and RNA probes, PCR primers, and anti-heparanase antibodies (heparanase specific molecular probes) can be applied to detect the heparanase gene and protein and hence for early diagnosis of micrometastases, autoimmune lesions, renal failure and atherosclerotic lesions using biopsy specimens, plasma samples, and body fluids.

Specificity and Advantages over other Reported Antibodies:

A variety of blood, tumor cells and certain normal cells have been shown to produce significant amounts of heparanase activity. The purification to homogeneity and characterization of mammalian heparanases has been difficult, primarily due to the lack of a convenient assay. Most reports contain only partial description with conflicting information. Oosta, et al. (22) described the purification of a human platelet heparanase with an estimated molecular mass of 134 kDa expressing an endoglucuronidase activity. Hoogewert, et al. (23) reported the purification of a 30 kDa human platelet heparanase which was shown to be an endoglucosaminidase that cleave both heparin and heparan sulfate essentially to disaccharides. They claimed that the holoenzyme consists of four subunits, each closely related to the CXC chemokines CTAPIII, NAP-2 and β-thromboglobulin (23). Freeman and Parish (24) have purified to homogeneity a 50 kDa platelet heparanase exhibiting endoglucuronidase activity. Likewise heparanase enzyme purified from human placenta and from hepatoma cell line (U.S. Pat. No. 5,362, 641) had a molecular mass of approximately 48 kDa. A similar molecular weight was determined by gel filtration analysis of partially purified heparanase enzymes isolated form human platelets, human neutrophils and mouse B16 melanoma cells (our unpublished data). In contrast, heparanase purified from B16 melanoma cells by Nakajima, et al. (9, 26) had a molecular weight of 96 kDa. The latter enzyme has been localized immunochemically to the cell surface and cytoplasm of human melanoma lesions using a polyclonal antiserum (26) and in tertiary granules in neutrophils using monoclonal antibodies (26a), both directed against a putative amino terminal sequence from purified B16F10 melanoma cell heparanase (26). However, the melanoma heparanase amino terminal sequence was found to be characteristic of a 94 kDa glucose-regulated protein (GRP94/ endoplasmin) that functions as a molecular chaperone which lacks heparanase activity (27). This result and a recent study using anti-endoplasmin antibody (28) suggest that the endoplasmin-like 98 kDa protein found in purified melanoma heparanase preparations is a contaminant (27, 28). This calls into question the previous heparanase immunolocalization studies carried out using the B 16 melanoma heparanase amino terminal peptide antiserum (26). Likewise, antiserum directed against the amino terminal sequence of CTAP III was applied to immunolocalize the heparanase enzyme in biopsy specimens of human prostate and breast carcinomas (29, 30). Again, the validity of the results is questionable, since the possibility that CTAP III is a contaminant of the platelet preparation was not excluded. First, attempts to express heparanase active CTAPIII/NAP2 protein were unsuccessful and the recombinant CTAPIII/ NAP2 chemokines failed to exhibit heparanase activity. Second, western blot analysis of the platelet enzyme purified by Freeman and Parish (24) with antibodies against human β-thromboglobulin or platelet factor-4 demonstrated that these and related proteins (e.g., CTAP-III and NAP-2) were not present in the purified platelet heparanase preparations (24). Moreover, while heparanase activity can be detected in purified preparations of β-thromboglobulin, it is probably due to contamination with the "classical" platelet heparanase since it exhibited an endo-beta-D-glucuronidase activity rather than an endoglucosaminidase activity (23), as reported by Hoogewerf et al. (Pikas et al. manuscript submitted for publication).

Our studies on the immunolocalization of CTAPIII in human biopsy specimens revealed a preferential localization of CTAP-III in cells (i.e., vascular endothelia cells, keratinocytes) that failed to express heparanase activity and vice versa. Finally, none of the sequences published by Hoogewerf et al (platelet CTAP-III/NAP-2) (23) or Jin et al. (B16 melanoma) (26) nor sequences of the bacterial heparin/ heparan sulfate degrading enzymes (hep I & III) (30a) were found in our recombinant human heparanase that was cloned and expressed on the basis of sequences derived from the purified human placenta and hepatoma heparanases.

Several years ago we prepared rabbit polyclonal antibodies directed against our partially purified preparation of human placenta heparanase. These antibodies, referred to in U.S. Pat. No. 5,362,641, were later found to be directed against plasminogen activator inhibitor type I (PAI-1) that was co-purified with the placental heparanase. These findings led to a modification of the original purification protocol to remove the PAI-1 contaminant.

Collectively, it is evident that so far no one had succeeded in eliciting anti-heparanase antibodies.

Unlike the above described information, both the polyclonal and monoclonal antibodies described hereinunder were raised, for the first time, against a purified, highly active, recombinant enzyme. As further shown below these antibodies specifically recognizes the heparanase enzyme in cell lysates and conditioned media and does not cross-react with β-thromboglobulin, NAP-2, PAI-1 or bacterial heparinases I and III. They do recognize the mouse B16-F10 heparanase, the human platelet heparanases, and the heparanase enzymes produced by several human tumor cell lines and Chinese hamster ovary (CHO) cells. By virtue of being produced against a purified recombinant enzyme and their specificity, these antibodies appear highly appropriate for diagnostic purposes such as immunohistochemistry of biopsy specimens and quantitative ELISA of body fluids (e.g., plasma, urine, pleural effusions, etc.). Similarly, as presented in the Examples section hereinunder, both the molecular probes for in situ determination of the tissue distribution of the hpa gene and the cDNA primers for detection of the hpa mRNA in normal and malignant cells of human origin (e.g., leukemia and lymphoma cells, melanoma cells) can be applied, for the first time, for diagnosis of early events in tumor progression, metastatic spread and response to treatment.

SUMMARY OF THE INVENTION

According to the present invention there are provided heparanase specific molecular probes and their use in use in research and medical applications including diagnosis and therapy.

According to further features in preferred embodiments of the invention described below, there is provided an antibody elicited by a heparanase protein or an immunogenical portion thereof, the antibody specifically binds heparanase.

According to still further features in the described preferred embodiments the heparanase protein is recombinant.

According to still further features in the described preferred embodiments the elicitation is through in vivo or in vitro techniques, the antibody having been prepared by a process comprising the steps of (a) exposing cells capable of producing antibodies to the heparanase protein or the immunogenical part thereof and thereby generating antibody producing cells; (b) fusing the antibody producing cells with myeloma cells and thereby generating a plurality of hybridoma cells each producing monoclonal antibodies; and (c) screening the plurality of monoclonal antibodies to identify a monoclonal antibody which specifically binds heparanase.

According to still further features in the described preferred embodiments the antibody is selected from the group consisting of a polyclonal antibody and a monoclonal antibody.

According to still further features in the described preferred embodiments the polyclonal antibody is selected from the group consisting of a crude polyclonal antibody and an affinity purified polyclonal antibody.

According to further features in preferred embodiments of the invention described below, there is provided an oligonucleotide comprising a nucleic acid sequence specifically hybridizable with heparanase encoding nucleic acid.

According to further features in preferred embodiments of the invention described below, there is provided a pair of polymerase chain reaction primers comprising a sense primer and an antisense primers, each of the primers including a nucleic acid sequence specifically hybridizable with heparanase encoding nucleic acid.

According to further features in preferred embodiments of the invention described below, there is provided an antisense nucleic acid (RNA or DNA) molecule comprising a nucleic acid sequence specifically hybridizable with heparanase messenger RNA.

According to further features in preferred embodiments of the invention described below, there is provided a sense nucleic acid (RNA or DNA) molecule comprising a nucleic acid sequence specifically hybridizable with heparanase antisense RNA.

According to further features in preferred embodiments of the invention described below, there is provided a method of in situ detecting localization and distribution of heparanase expression in a biological sample comprising the step of reacting the biological sample with a detectable heparanase specific molecular probe and detecting the localization and distribution of the detectable heparanase specific molecular probe.

According to further features in preferred embodiments of the invention described below, there is provided a method of detecting heparanase expression in a biological sample comprising the step of reacting the biological sample with a detectable heparanase specific molecular probe and detecting said detectable heparanase specific molecular probe. Protein and nucleic acid dot blot application are envisaged.

According to still further features in the described preferred embodiments the biological sample is selected from the group consisting of cells and tissues.

According to still further features in the described preferred embodiments the biological sample is malignant.

According to still further features in the described preferred embodiments the malignancy is selected from the group consisting of a solid tumor and a hematopoietic tumor.

According to still further features in the described preferred embodiments the solid tumor is selected from the group consisting of carcinoma, adenocarcinoma, squamous cell carcinoma, teratocarcinoma, mesothelioma and melanoma, and further wherein the hematopoietic tumor is selected from the group consisting of lymphoma and leukemia.

According to still further features in the described preferred embodiments the solid tumor is a primary tumor, or a metastasis thereof, and is originated from an organ selected from the group consisting of liver, prostate, bladder, breast, ovary, cervix, colon, skin, intestine, stomach, uterus, pancreas.

According to still further features in the described preferred embodiments the detectable heparanase specific molecular probe is selected from the group consisting of a nucleic acid sequence hybridizable with heparanase encoding nucleic acid and an anti-heparanase antibody capable of specifically binding heparanase.

According to still further features in the described preferred embodiments the nucleic acid sequence hybridizable with heparanase encoding nucleic acid is selected from the group consisting of a synthetic oligonucleotide, an antisesnse heparanase RNA and heparanase DNA labeled by a detectable moiety.

According to further features in preferred embodiments of the invention described below, there is provided a method of detecting heparanase protein in a body fluid of a patient comprising the steps of reacting the body fluid with an anti-heparanase antibody and monitoring the reaction.

According to still further features in the described preferred embodiments the body fluid is selected from the group consisting of plasma, urine, pleural effusions and saliva.

According to still further features in the described preferred embodiments the body fluid is of a patient suffering from a condition selected from the group consisting of cancer, renal disease and diabetes.

According to still further features in the described preferred embodiments the renal disease is associated with diabetes.

According to still further features in the described preferred embodiments the anti-heparanase antibody is selected from the group consisting of a monoclonal antibody and a poly clonal antibody.

According to still further features in the described preferred embodiments reacting the body fluid with the anti-heparanase antibody is effected in solution.

According to still further features in the described preferred embodiments reacting the body fluid with the anti-heparanase antibody is effected on a substrate capable of adsorbing proteins present in the body fluid.

According to still further features in the described preferred embodiments the body fluid is of a patient suffering from myeloma, breast carcinoma, metastatic breast carcinoma, hemorrhagic nephritis, nephrotic syndrome, normoalbuminuric type I diabetes, microalbuminuric type I diabetes, kidney disorder, inflammation, sepsis, inflammatory and autoimmune disease.

According to further features in preferred embodiments of the invention described below, there is provided a method of detecting the presence, absence or level of heparanase transcripts in a biological sample comprising the steps of (a) extracting messenger RNA from the biological sample, thereby obtaining a plurality of messenger RNAs; (b) reverse transcribing the plurality of messenger RNAs into a plurality of complementary DNAs; (c) contacting the plurality of complementary DNAs with a pair of heparanase specific polymerase chain reaction primers, nucleoside triphosphates and a thermostable DNA polymerase; (d) performing a polymerase chain reaction; and (e) detecting the presence, absence or level of the polymerase chain reaction product.

According to further features in preferred embodiments of the invention described below, there is provided a method of detecting heparanase messenger RNA in a biological sample comprising the steps of reverse transcribing the messenger RNA into complementary DNA, contacting the complementary DNA with polymerase chain reaction oligonucleotides hybridizable to heparanase encoding nucleic acid, performing a polymerase chain reaction and monitoring for heparanase specific polymerase chain reaction products.

According to further features in preferred embodiments of the invention described below, there is provided a method of detecting the presence, absence or level of heparanase protein in a biological sample comprising the steps of (a) extracting proteins from the biological sample, thereby obtaining a plurality of proteins; (b) size separating the proteins; (c) interacting the size separated proteins with an anti-heparanase antibody; and (d) detecting the presence, absence or level of the interacted anti-heparanase antibody.

According to still further features in the described preferred embodiments the anti-heparanase antibody is selected from the group consisting of a polyclonal antibody and a monoclonal antibody.

According to still further features in the described preferred embodiments the size separation is effected by electrophoresis.

According to further features in preferred embodiments of the invention described below, there is provided a method of targeted drug delivery to a tissue of a patient, the tissue expressing heparanase, the method comprising the steps of providing a complex of a drug directly or indirectly linked to an anti-heparanase antibody and administering the complex to the patient.

According to further features in preferred embodiments of the invention described below, there is provided a method of treating a patient having a condition associated with heparanase expression comprising the step of administering an anti-heparanase antibody to the patient.

It is an object of the present invention to use a heparanase specific molecular probe for detection of the presence, absence or level of heparanase expression.

It is another object of the present invention to use a heparanase specific molecular probe for therapy of a condition associated with expression of heparanase.

It is yet another object of the present invention to use a heparanase specific molecular probe for quantification of heparanase in a body fluid.

It is still another object of the present invention to use a heparanase specific molecular probe for targeted drug delivery.

It is another object of the present invention to use a heparanase specific molecular probe as a therapeutic agent.

The present invention successfully addresses the shortcomings of the presently known configurations by providing a variety of heparanase specific molecular probes which can be used for research and medical applications including diagnosis and therapy.

BRIEF DESCRIPTION OF THE DRAWINGS

The file of this patent contains at least one drawing executed in color photograph. Copies of this patent with color photographs will be provided by the Patent and Trademark Office upon request and payment of necessary fees.

The invention herein described, by way of example only, with reference to the accompanying drawings, wherein:

FIGS. 2a–b demonstrate heparanase activity expressed by human breast carcinoma cell lines with different metastatic potentials. Breast carcinoma cell lysates of the above described cell lines were incubated (24 hours, 37° C., pH 6.2) with $^{35}$S-HSPG isolated from intact subendothelial ECM. Heparanase mediated conversion of the heparan sulfate substrate (peak I) into low MW degradation fragments (peak II) was analyzed by gel filtration on Sepharose 6B. Expression of the human hpa gene correlates with heparanase activity and metastasis in experimental animals.

FIGS. 3a–f demonstrate detection of hpa mRNA by in situ hybridization in specimens of normal and malignant human breast tissue with antisense heparanase RNA probe: invasive carcinoma of the breast, pre-malignant fibrocystic breast tissue, adenocarcinoma of the breast, invasive breast carcinoma surrounding the area of tumor necrosis (not stained), normal breast tissue-reduction mammoplasty (antisense hpa probe), and normal breast tissue-reduction mammoplasty (control sense probe), respectively.

FIGS. 9a–f demonstrate detection of hpa mRNA by in situ hybridization in specimens of human malignant melanoma and normal nevus.

FIGS. 9a, c and d—metastatic human melanoma (3 different patients),

FIG. 9b—non malignant nevus tissue. Labeling is not seen in the nevus tissue, as compared to intense staining of the metastatic melanoma.

FIGS. 9e and f—same sections as in Figures c and d stained with hematoxylin-eosine.

FIGS. 10a–f demonstrate detection of hpa mRNA by in situ hybridization in specimens of normal and malignant human liver. Hepatocellular carcinoma (×200), hepatocellular carcinoma (×1000), liver adenocarcinoma, normal adult liver, embryonic liver and control sense staining of embryonic liver are shown respectively. Labeling is not seen in normal liver cells as compared to intense staining of embryonic and malignant liver cells.

FIGS. 11a–f demonstrate detection of hpa mRNA by in situ hybridization in specimens of normal and malignant human tissues. Adenocarcinoma of the ovary, normal ovary, squameous cell carcinoma of the cervix, normal cervix, colon adenocarcinoma and normal small intestine are shown respectively.

FIGS. 12a–f demonstrate detection of hpa mRNA by in situ hybridization in specimens of various human tumors. Positive staining of the hpa gene was clearly seen in adenocarcinoma of the stomach, teratocarcinoma, well differentiated endometrial adenocarcinoma, adenocarcinoma of the pancreas, mesothelioma, FIGS. 12a–e, respectively. Control, sense staining of human mesothelioma is shown in FIG. 12f.

Proteins were separated on 8–16% gradient gel. Detection was performed by ECL (Amersham) according to the manufacturer's instructions. Size in kDa is shown to the right, as was determined using prestained SDS-PAGE standards, Bio-Rad, CA.

Figure 20:
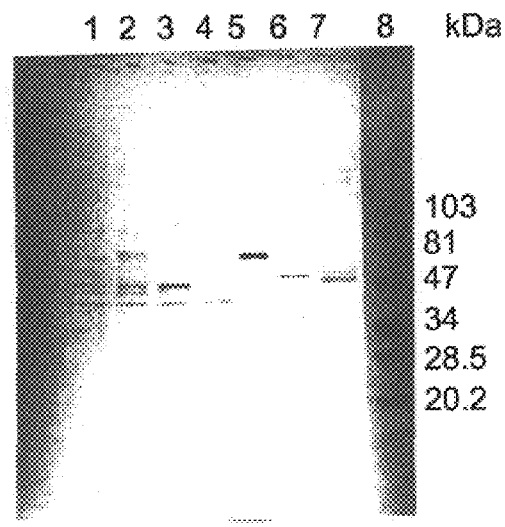

FIG. 20 demonstrates Western blot of recombinant and native heparanases from various origins using supernatant of hybridoma HP-117. Lanes 1 and 2, 293 human kidney cells non-transfected and transfected with hpa-pCDNA, respectively (15 μg), lane 3, CHO cells stably transfected with pShpa (40 μg), lane 4, mock transfected CHO cells (40 μ), lane 5, purified recombinant heparanase produced by baculovirus infected insect cells (50 ng), lane 6, cell extracts of E. coli expressing recombinant heparanase (50 ng), lane 7, cell extract of human platelets (100 μg), lane 8, prestained SDS-PAGE standard, Bio-Rad, CA. Proteins were separated on 4–20% gradient SDS-PAGE and transferred to a nylon membrane (Amersham). Membrane was incubated with supernatant of hybridoma Hp117 and detection was performed with alkaline phosphatase conjugated anti-mouse IgG antibodies.

Figures 21A, 21B:
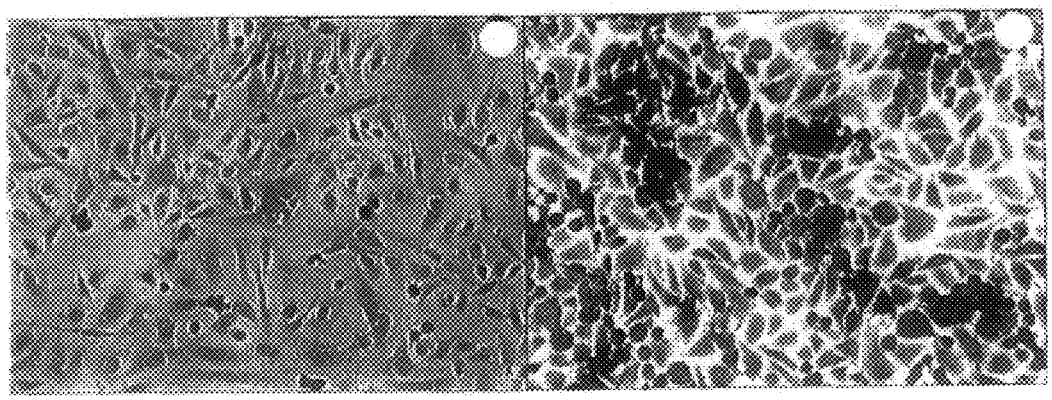

FIGS. 21a–b demonstrate immunostaining of heparanase in CHO cells with polyclonal antibodies. CHO cells transfected with the full length hpa gene (21a) were tested for overexpression of heparanase. Staining is detected in the cytoplasm of transfected cells. In non transfected CHO cells (21b), no staining of heparanase is detected.

FIGS. 22a–b demonstrate immunostaining of heparanase in CHO cells with monoclonal antibody HP-130. CHO cells transfected with the full length hpa gene (22a) were tested for overexpression of heparanase. Staining is detected in the cytoplasm of transfected cells. In non transfected CHO cells (22b), no staining of heparanase is detected.

FIGS. 23a–c demonstrate immunostaining of heparanase in blood smears from normal donor with monoclonal antibody HP-92. Heparanase is found in the cytoplasm of neutrophils (23a) and platelets (23c) but is not detected in lymphocytes (23b) and monocytes (23c).

DESCRIPTION OF THE PREFERRED EMBODIMENTS

The present invention is of heparanase specific molecular probes which can be used in research and medical applications. Specifically, the present invention can be used for the detection and monitoring of malignancies, metastasis and other, non-malignant conditions, efficiency of therapeutic treatments, targeted drug delivery and therapy, using heparanase specific molecular probes, such as anti-heparanase antibodies (both poly- and monoclonal) and heparanase gene (hpa) derived nucleic acids, including, but not limited to, PCR primers, antisense oligonucleotide probes, antisense RNA probes, DNA probes and the like.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As shown in the Examples section below heparanase specific antibodies and/or nucleic acids reveals in situ expression (protein and/or messenger RNA) of heparanase in a variety of cells and tissues, especially in malignant cells and tissues, wherein the degree of expression corroborates with metastasis.

Therefore, according to one aspect of the present invention there is provided a method of in situ detecting localization and distribution of heparanase expression in a biological sample. The method comprises the step of reacting the biological sample with a detectable heparanase specific molecular probe and detecting the localization and distribution of the detectable heparanase specific molecular probe.

According to another aspect of the present invention, there is provided a method of detecting heparanase expression in a biological sample. The method comprises the step of reacting the biological sample with a detectable heparanase specific molecular probe and detecting the detectable heparanase specific molecular probe. Protein and nucleic acid dot blot application are envisaged.

As used herein in the specification and in the claims section below, the term "heparanase expression" refers mainly to the processes of transcription and translation, resulting in a catalytically active heparanase having endoglycosidase hydrolyzing activity which is specific for heparin or heparan sulfate proteoglycan substrates, as opposed to the activity of bacterial enzymes (heparinase I, II and III) which degrade heparin or heparan sulfate by means of β-elimination.

As used herein in the specification and in the claims section below, the term "biological sample" refers to cells and tissues, including, but not limited to cancer cells and tissues. The term further relates to body fluids, as further detailed below.

As used herein in the specification and in the claims section below, the term "detectable heparanase specific molecular probe" and its equivalent term "detectable heparanase molecular probe" both refer to a nucleic acid sequences hybridizable with heparanase encoding nucleic acid or to an anti-heparanase antibody capable of specifically binding heparanase. The nucleic acid sequence hybridizable with heparanase encoding nucleic acid is, for example, a synthetic oligonucleotide, an antisesnse heparanase RNA or heparanase DNA, and it is preferably labeled by the detectable moiety.

As used herein in the specification and in the claims section below, the term "detectable moiety" refers to any atom, molecule or a portion thereof, the presence, absence or level of which is directly or indirectly monitorable. One example include radioactive isotopes. Other examples include (i) enzymes which can catalyze color or light emitting (luminescence) reactions and (ii) fluorophores. The detection of the detectable moiety can be direct provided that the detectable moiety is itself detectable, such as, for example, in the case of fluorophores. Alternatively, the detection of the detectable moiety can be indirect. In the latter case, a second moiety reactable with the detectable moiety, itself being directly detectable is preferably employed. The detectable moiety may be inherent to the molecular probe. For example, the constant region of an antibody can serve as an indirect detectable moiety to which a second antibody having a direct detectable moiety can specifically bind.

As used herein in the specification and in the claims section below, the term "antibody" refers to any monoclonal or polyclonal immunoglobulin, or a fragment of an immunoglobin such as sFv (single chain antigen binding protein), Fab1 or Fab2. The immunoglobulin could also be a "humanized" antibody, in which murine variable regions are fused to human constant regions, or in which murine complementarity-determining regions are grafted onto a human antibody structure (Wilder, R. B. et al., J. Clin. Oncol., 14:1383–1400, 1996). Unlike mouse or rabbit antibodies, "humanized" antibodies often do not undergo an undesirable reaction with the immune system of the subject. The terms "sFv" and "single chain antigen binding protein" refer to a type of a fragment of an immunoglobulin, an example of which is sFv CC49 (Larson, S. M. et al., Cancer, 80:2458-68, 1997).

According to one embodiment of the invention the biological sample is malignant, e.g., it is a solid tumor or hematopoietic tumor sample. The solid tumor can, for example, be of the types: carcinoma, adenocarcinoma, squameous cell carcinoma, teratocarcinoma, mesothelioma or melanoma, which are shown hereinunder in the Examples section to express heparanase in good correlation to the degree of metastasis. The hematopoietic tumor can, for example, be lymphoma or leukemia.

In some embodiments of the present invention the solid tumor is a primary tumor, or a metastasis thereof, and it originates from an organ such as, for example, liver, prostate, bladder, breast, ovary, cervix, colon, skin, intestine, stomach, uterus (including embryo) and pancreas.

As shown in the Examples section below, it was further found that body fluids (e.g., urine) of patients with certain conditions include catalitically active heparanase. These conditions include myeloma, breast carcinoma, metastatic breast carcinoma, hemorrhagic nephritis, nephrotic syndrome, normoalbuminuric type I diabetes, microalbuminuric type I diabetes, kidney disorder, inflammation, sepsis, inflammatory and autoimmune disease.

Therefore, according to another aspect of the present invention there is provided a method of detecting heparanase protein in a body fluid of a patient. The method comprises the steps of reacting the body fluid with an anti-heparanase antibody, either poly or monoclonal antibody, and monitoring the reaction. The body fluid is, for example, plasma, urine, pleural effusions or saliva. Monitoring the reaction may be effected by having the antibody labeled with a detectable moiety, or to use its constant region as an inherent detectable moiety, to which a second antibody which includes a detectable moiety can specifically bind.

Urine heparanase was detected in patients suffering from conditions such as cancer, renal disease and diabetes. In some cases the renal disease was associated with diabetes.

According to a preferred embodiment of the present invention reacting the body fluid with the anti-heparanase antibody is effected in solution. Alternatively, reacting the body fluid with the anti-heparanase antibody is effected on a substrate capable of adsorbing proteins present in the body fluid, all as well known in the art of antibody based diagnosis.

As further shown in the Examples section below, RT-PCR proves useful in detecting the presence, absence or level of heparanase transcripts in various biological samples.

Therefore, according to another aspect of the present invention there is provided a method of detecting the presence, absence or level of heparanase transcripts in a biological sample. The method comprises the following steps. First, messenger RNA (e.g., as a component of total RNA) is extracted from the biological sample, thereby a plurality of messenger RNAs are obtained. Second, the plurality of messenger RNAs are reverse transcribed into a plurality of complementary DNAs. Third, the plurality of complementary DNAs are contacted with a pair of heparanase specific polymerase chain reaction (PCR) primers, nucleoside triphosphates and a thermostable DNA polymerase (e.g., Thermophilus aquaticus DNA polymerase, native or recombinant) and a polymerase chain reaction is performed by temperature cycling, as well known in the art. Finally, the presence, absence or level of the polymerase chain reaction product is detected, e.g., by gel electrophoresis, by monitoring the incorporation of a detectable moiety into the product or any other applicable way, all as well known in the art.

As further shown in the Examples section below, protein blots and anti-heparanase antibodies prove useful in detecting the presence, absence or level of heparanase protein in various biological samples.

Therefore, further according to the present invention there is provided a method of detecting the presence, absence or level of heparanase protein in a biological sample. The method comprises the following steps. First, proteins are extracted from the biological sample, thereby a plurality of proteins are obtained. The protein extract may be a crude extract and can also include non-proteinacious material. Second, the proteins are size separated, e.g., by electrophoresis, gel filtration etc. Fourth, the size separated proteins are interacted with an anti-heparanase antibody, either poly or monoclonal antibody. Finally, the presence, absence or level of the interacted anti-heparanase antibody is detected. In case of gel electrophoresis the interaction with the antibody is typically performed following blotting of the size separated proteins onto a solid support (membrane).

In many cases it was shown that directly or indirectly (e.g., via liposomes) linking a drug (e.g., anti cancerous drug, such as, for example radio isotopes) to an antibody which recognized a protein specifically expressed by a tissue sensitive to the drug and administering the antibody-drug complex to a patient, results in targeted delivery of the drug to the expressing tissue.

Therefore, according to yet another aspect of the present invention there is provided a method of targeted drug delivery to a tissue of a patient, the tissue expressing heparanase. The method comprises the steps of providing a complex of a drug directly or indirectly linked to an anti-heparanase antibody and administering the complex to the patient. External radio imaging is also envisaged, wherein the drug is replaced with an imageable radio isotope. Endoscopic or laparoscopic imaging is also envisaged. In the latter cases the drug is typically replaced by a fluorescence or luminescence substance. These procedures may, for example, be effective in finding/destroying micrometastases.

In other cases, it was shown that administering an antibody capable of binding epitopes associated with certain tissues provide means of destroying such tissues by an elicited immune response.

Therefore, according to another aspect of the present invention there is provided a method of treating a patient having a condition associated with heparanase expression. The method comprises the step of administering an anti-heparanase antibody to the patient.

Further according to the present invention there is provided an antibody elicited by a heparanase protein (e.g., recombinant) or an immunogenical portion thereof, the antibody specifically binds heparanase. The antibody can be a poly or monoclonal antibody. If it is poly clonal and produced in vivo, it is preferably affinity purified, however crude antibody preparations are also applicable, all as shown and described in more detail in the Examples section hereinunder.

Preferably, the elicitation of the antibody is through in vivo or in vitro techniques, the antibody having been prepared by a process comprising the steps of, first, exposing cells capable of producing antibodies to the heparanase protein or the immonogenical part thereof and thereby generating antibody producing cells. second, fusing the antibody producing cells with myeloma cells and thereby generating a plurality of hybridoma cells each producing monoclonal antibodies, and third, screening the plurality of monoclonal antibodies to identify a monoclonal antibody which specifically binds heparanase.

Further according to the present invention there is provided an oligonucleotide comprising a nucleic acid sequence specifically hybridizable with heparanase encoding nucleic acid, be it heparanase DNA or RNA. The oligonucleotide may include natural nucleotides and/or nucleotide analogs, such as, but not limited to phosphorothioated analogs. Such oligonucleotides are readily synthesized provided that the sequence is known. Such oligonucleotides can be deduces, for example, from SEQ ID NOs: 1 and 3.

Further according to the present invention there are provided an antisense nucleic acid (RNA or DNA) molecule comprising a nucleic acid sequence specifically hybridizable with heparanase messenger RNA and a sense nucleic acid (RNA or DNA) molecule comprising a nucleic acid sequence specifically hybridizable with heparanase antisense RNA.

EXAMPLES

Reference is now made to the following examples, which together with the above descriptions, illustrate the invention in a non limiting fashion.

Experimental Methods and Materials

Cells:

Cultures of bovine corneal endothelial cells (BCECs) were established from steer eyes as previously described (19, 31). Stock cultures were maintained in DMEM (1 gram glucose/liter) supplemented with 10% newborn calf serum, 5% fetal calf serum (FCS). bFGF (1 ng/ml) was added every other day during the phase of active cell growth (14, 15).

Preparation of Sulfate Labeled Substrates:

BCECs (second to fifth passage) were plated into 35 mm tissue culture plates at an initial density of $2 \times 10^5$ cells/ml and cultured in DMEM supplemented with 10% FCS and 5% dextran T-40 for 12 days. $Na_2^{35}SO_4$ (25 μCi/ml) was added on day 1 and 5 after seeding and the cultures were incubated with the label without medium change. The subendothelial ECM was exposed by dissolving (5 min, room temperature) the cell layer with PBS containing 0.5% Triton X-100 and 20 mM $NH_4OH$, followed by four washes with PBS. The ECM remained intact, free of cellular debris and firmly attached to the entire area of the tissue culture dish (14, 15, 20).

To prepare soluble sulfate labeled proteoglycans (peak I material), the ECM was digested with trypsin (25 μg/ml, 6 hours, 37° C.), the digest was concentrated by reverse dialysis, applied onto a Sepharose 6B gel filtration column and the high molecular weight material (Kav<0.2, peak I) was collected (32). More than 80% of the labeled material was shown to be composed of heparan sulfate proteoglycans (11).

Heparanase Activity:

Cells ($1 \times 10^6$/35-mm dish), cell lysates or conditioned medium were incubated on top of $^{35}$S-labeled ECM (18 hours, 37° C.) in the presence of 20 mM phosphate or phosphate citrate buffer (pH 6.2). Cell lysates and conditioned media were also incubated with sulfate labeled peak I material (10–20 μl). The incubation medium was collected, centrifuged (18,000 g, 4° C., 3 min), and sulfate labeled material was analyzed by gel filtration on a Sepharose CL-6B column (0.9×30 cm). Fractions (0.2 ml) were eluted with PBS at a flow rate of 5 ml/hour and counted for radioactivity using Bio-fluor scintillation fluid. The excluded volume ($V_o$) was marked by blue dextran and the total included volume ($V_t$) by phenol red. The latter was shown to comigrate with free sulfate (11, 20). Degradation fragments of HS side chains were eluted from Sepharose 6B at 0.5<Kav<0.8 (peak II) (11, 20). A nearly intact HSPG released from ECM by trypsin was eluted next to $V_o$ (Kav<0.2, peak I). Recoveries of labeled material applied on the columns ranged from 85 to 95% in different experiments.

Construction of Heparanase Expression Vector:

A BamHI-KpnI 1.3 kb fragment (nucleotides 450–1721 of the hpa sequence, SEQ ID NOs: 1 and 3, U.S. patent application Ser. No. 08/922,170) was cut out from pfasthpa and cloned into pRSET-C bacterial expression vector (Invitrogen). The resulting recombinant plasmid pRSEThpaBK encodes a fusion protein comprised of His tag, a linker sequence and amino acids 130–543 of the heparanase protein (SEQ ID NOs: 2 and 3).

A 1.6 kb fragment of hpa cDNA was amplified from pfasthpa (a hpa cDNA cloned in pfastBac, see U.S. patent Ser. No. 08/922,170), by PCR using specific sense primer: (Hpu-550Nde)-5'-CGCATATGCAGGACGTCGTG GACCTG-3'(SEQ ID NO:4) and a vector specific antisense primer: (3'pFast) 5'-TATGATCCTCTAGTACTTCTCGAC-3' (SEQ ID NO:5). The upper primer introduced an NdeI site and an ATG codon preceding nucleotide 168 of hpa. The PCR product was digested by NdeI and BamHI and its sequence was confirmed. pRSEThpaBK was digested with NdeI and BamHI and ligated with the NdeI-BamHI hpa fragment. The resulting plasmid, designated pRSEThpaS1, encoded an open reading frame of 508 amino acids (36–543) of the heparanase protein, lacking the N-terminal 35 amino acids which are predicted to be a signal peptide. Expression constructs were introduced into E. coli BL21(DEL3)pLysS cells (Stratagene), according to supplier's protocol.

Preparation of Antigen:

E. coli cells harboring the recombinant plasmid were grown at 37° C. overnight in Luria broth containing ampicillin and chloramphenicol. Cells were diluted ⅟₁₀ in the same medium, and the cultures were grown to an OD600 of approximately 0.5. Isopropyl-thiogalactoside (IPTG) (Promega) was added to a final concentration of 1 mM and the culture was incubated at 37° C. for 3 hours. Cells from induced cultures were cooled on ice, sedimented by centrifugation at 4,000× g for 20 minutes at 4° C., and resuspended in 0.5 ml of cold phosphate-buffered saline (PBS). Cells were lysed by sonication, and cell debris was sedimented by centrifugation at 10,000× g for 20 minutes. The resulting pellet was analyzed by 10% SDS-PAGE. The gel was stained with 1x PBS coomassie blue and the band of 45 kDa which contained the recombinant heparanase was cut out and crashed through a needle (21G) attached to a syringe. For immunization of mice, the crashed gel was incubated in PBS overnight at 4° C. and the protein diffused into the buffer was collected. Rabbits ware injected with gel homogenate.

The 55 kDa protein (508 amino acids) was purified from E. coli inclusion bodies by preparative SDS-PAGE, using a Model 491 Prep Cell (Bio-Rad) which is designed to purify proteins from complex mixtures by continuous elution electrophoresis. This antigen was used for ELISA screening.

Immunization—Polyclonal Antibodies:

Two rabbits (designated 7640 and 7644) were immunized each with 200 µg of protein emulsified with equal volume of complete Freund's adjuvant. An equal amount of protein emulsified with incomplete Freund's was injected to each rabbit two weeks following the first injection and again after another four weeks. Ten days after the third injection the rabbits were bled and serum was examined for reactivity with recombinant heparanase. Four weeks after bleeding another boost was injected and 10 days later blood was collected.

Immunization—Monoclonal Antibodies:

6 to 8 weeks old female Balb/C mice were each immunized intradermally with 50 µg recombinant heparanase emulsified in 50 µl PBS complete Freund's adjuvant. Two to three weeks later the same amount of the emulsion was injected subcutaneously or intradermally at multiple sites in incomplete Freund's adjuvant. After 3 weeks 25 µg antigen in aqueous solution was injected intrapertonealy. 7–10 days later animals were bled and the titer of the relevant antibodies was determined. 3–4 weeks after the last boost, one or two animals were injected intraperitoneal with 20 µg of soluble antigen (in PBS) and 3–4 days later spleens were removed.

Fusion and Cloning:

The spleens of immunized mice were ground, splenocytes were harvested and fused with the NSO myeloma cells by adding 41% PEG. Hybridoma cells were grown in HAT-selective DMEM growth media containing 15% (v/v) HS (Beit Haemek), 2 mM glutamine, Pen-Strep-Nystatin solution (Penicillin: 10,000 units/ml, Streptomycin: 10 mg/ml, Nystatin: 1,250 units/ml), at 37° C. in 8% $CO_2$ containing atmosphere. Hybridoma cells were cloned by limiting dilution. Hybridomas producing Mabs to human heparanase were identified by reactivity with solid-phase immobilized human heparanase.

ELISA:

Falcon polyvinyl plates were coated with 50 ng/well of baculovirus derived human heparanase (native) and 100 ng/well of E. coli derived human heparanase (55 kDa-non-active) in PBS (pH 7.2) overnight at 40° C. Hybridoma tissue culture supernatants were added to the wells, and incubated at room temperature for 2 hours. Binding of Mabs was then detected by incubation with HRP-conjugated goat anti mouse IgG (Fab specific) (Sigma), followed by development in o-phenylenediamine substrate (Sigma) and measurement of absorbencies at 450 nm. PBS with 0.05% Tween was used to wash the plates between incubations. Polyclonal rabbit anti human heparanase was used as positive control and negative control included coating with PBS or irrelevant supernatant.

Affinity Purification of Polyclonal Antibodies:

200 µg of recombinant heparanase were separated on 10% SDS-PAGE. Following electrophoresis protein was transferred to a nitrocellulose membrane (Schleicher & Scuell). Membrane was stained with Ponceau S and the heparanase band was cut out. The membrane strip was blocked for 2 hours in TBS containing 0.02% Tween 20 and 5% skim milk. Antiserum was diluted 1:3 in blocking solution and incubated with the membrane for 16 hours. Membrane strip was washed with 0.15 M NaCl for 20 minutes and then with PBS for additional 20 minutes. Antibodies were eluted with 0.2 M glycine, 1 mM EDTA pH 2.8 for 20 minutes at room temperature, and then neutralized by addition of 0.1 volumes of 1 M Tris pH 8.0 and 0.1 volumes of 10× PBS. $NaNO_3$ was added to a final concentration of 0.02%

Western Blot:

Proteins were separated on 4–20% or 8–16% polyacrylamide ready gradient gels (Novex). Following electrophoresis proteins were transferred to Hybond-P nylon membrane (Amersham) (350 mA/100V for 90 minutes). Membranes were blocked in TBS containing 0.02% Tween 20 and 5% skim milk for 1–16 hours, and then incubated with antisera diluted in blocking solution. Blots were then washed in TBS-Tween, incubated with appropriate HRP-conjugated anti mouse/anti rabbit IgG, and developed using ECL reagents (Amersham) according to the manufacturer's instructions. Alternatively, an alkaline phosphatase conjugated anti-mouse/anti-rabbit IgG antibodies were used as secondary antibodies and blots were developed with FAST™ BCIP/NBT (Sigma) according to the supplier's instructions.

Expression of the Heparanase Gene in Various Cell Types and Tissues (RT-PCR):

RT-PCR was applied to evaluate the expression of the hpa gene by various cell types. For this purpose, total RNA was reverse transcribed and amplified, using the following cDNA primers: Human hpa—Hpu-355

```
5'-TTCGATCCCAAGAAGGAATCAAC-3'    (SEQ ID NO:6) and Hpl-229-
5'-GTAGTGATGCCATGTAACTGAATC-3'   (SEQ ID NO:7).
```

Expression Pattern of the Heparanase Gene Transcript (In situ Hybridization).

In situ hybridization enables determination of the distribution of hpa transcripts in normal and malignant tissues. For this purpose, thin sections of biopsy specimens were processed for in situ hybridization and hybridized with an antisense RNA probe to the hpa gene. The experiments have the resolution power to unambiguously identify the expressing cell type, be they tumor cells, tissue macrophages, mast cells or platelets. Sections were treated with proteinase K to expose the target RNA and to block non specific binding sites before addition of the probe (34). For in situ hybridization, two digoxigenin labeled probes were prepared, one in the sense direction and the other in the anti-sense direction. They were both transcribed from a fragment of about 624 bp of the hpa cDNA sequence (nucleotides 728–1351, SEQ ID NOs: 1 and 3) cloned in to the EcoRI-HindIII sites of the transcription vector pT3T7-Pac (a modified vector derived from pT3T7, Pharmacia), using T3 (for antisense) or T7 (for sense) RNA polymerase, according to the suppliers protocol. Slides were hybridized under appropriate conditions with the labeled probe and the hybridized probe is visualized using colorimetric reagents (NBT & BCIP) (34). Reactions were stopped when the desired intensity has been reached.

In situ Detection of Heparanase by Antibodies:

hpa-transfected and non transfected CHO cells were plated on 8-chamber tissue culture slides (Nunc). Cells were fixed in 95% ethanol, 5% acetic acid for 5 minutes at −20° C. Cells were permeabilized using permeabilization buffer (20 mM HEPES, pH 7.4; 300 mM Sucrose; 50 mM NaCl; 3 mM $MgCl_2$; 0.5% Triton X-100) for 4 minutes at 4° C. Endogenous peroxidases were blocked using 0.3% $H_2O_2$ in methanol and non specific binding sites were blocked using 5% horse serum in PBS. Monoclonal anti-heparanase antibody (supernatant of hybridoma) was applied and incubated with the cells overnight at room temperature. Antibody was washed away and biotinylated secondary antibody (horse-anti mouse, Vector, Vectastain ABC system) was added for 30 minutes at room temperature. Immunostaining was detected using Di Amino Benzidine and $H_2O_2$ (Sigma tablets) until desired staining-intensity was achieved. Slides were counterstained with Mayer's hematoxylin. Immunostaining with polyclonal antibodies was performed under the same conditions, affinity purified antibody was used at 1:500 dilution. Biotinylated horse anti-rabbit was used as a secondary antibody (Vector, Vectastain ABC system). Blood smears were prepared from a healthy donor. Fixation and staining were performed as described above.

Experimental Results

Figure 1:
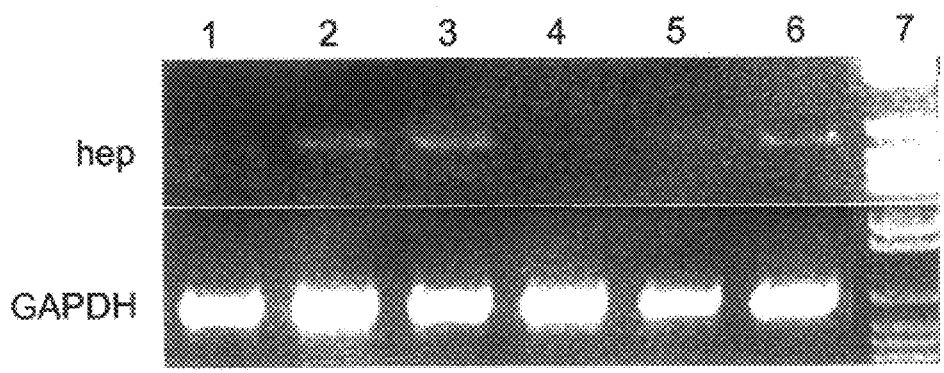
FIG. 1 demonstrates the expression of the human heparanase gene by human breast carcinoma cell lines with different metastatic potentials. Total RNA was isolated and subjected to semi quantitative RT-PCR (28 cycles) using human heparanase primers (hep) and primers for the GAPDH housekeeping gene. Reactions without reverse transcriptase demonstrated no amplification of genomic DNA contamination in the RNA samples (not shown). Lane 1, Non metastatic MCF-7 cells, lane 2, moderate metastatic MDA-231 cells, lane 3, highly aggressive MDA-435 cells, lane 4, minimal metastatic ZR-75 cells, lane 5, moderate metastatic MCF-ANeoT cells, lane 6, highly metastatic MCF-$T_6$ 3B cells; lane 7, DNA molecular weight marker VI (Boehringer Mannheim).
Figure 2A:
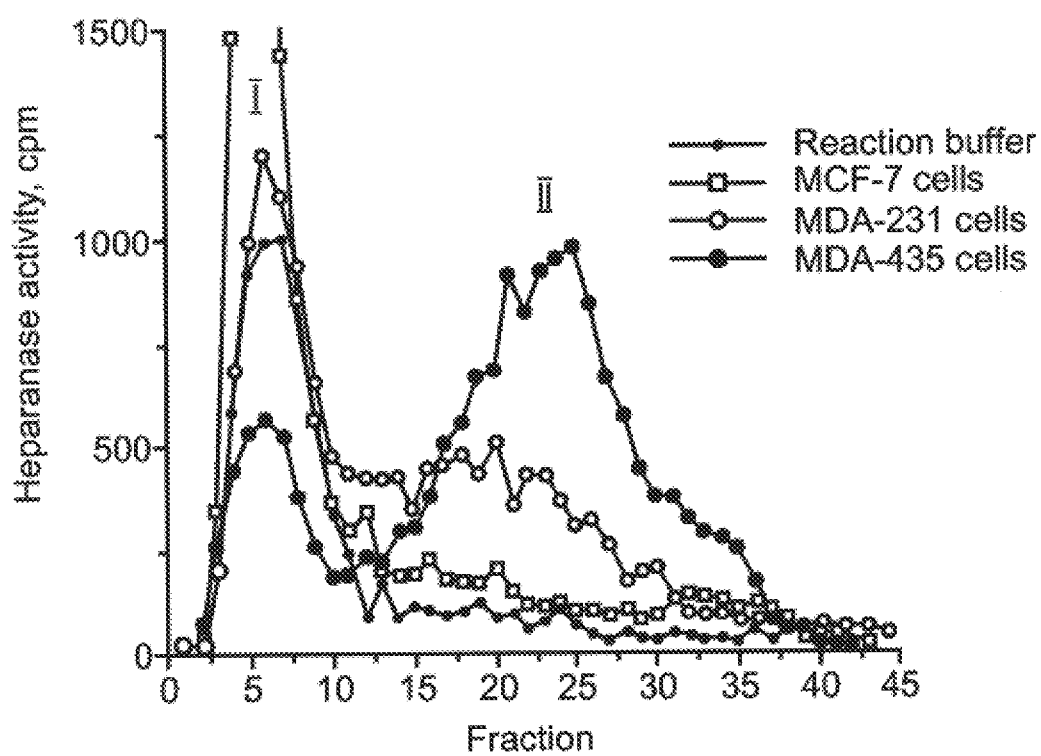

Differential Expression of the hpa Gene in Human Breast Carcinoma and Breast Carcinoma Cell Lines:

Semi-quantitative RT-PCR was applied to evaluate the expression of the hpa gene by human breast carcinoma cell lines exhibiting different degrees of metastasis (35, 36). While the non-metastatic MCF-7 breast carcinoma line failed to express the expected 585 bp cDNA of the hpa gene (FIG. 1, lane 1), moderate (MDA 231, FIG. 1, lane 2) and highly (MDA 435, lane 3) metastatic breast carcinoma cell lines exhibited a marked increase in hpa gene expression. The differential expression of the hpa gene was reflected by a similar differential pattern of heparanase activity. As demonstrated in FIG. 2a, lysates of MCF-7 cells exhibited little or no heparanase activity, as compared to a moderate and high activity expressed by MDA-231 and MDA-435 cells, characterized by moderate and high metastatic potential in nude mice, respectively.

The same pattern of hpa gene expression and heparan sulfate degrading activity was observed in another model of breast cancer. While the ZR75 (=MCF10A) displastic breast cell line originated from fibrocystic breast epithelial cells showed little or no expression of the hpa gene (FIG. 1, lane 4), Ha-ras transfected ZR75 cell line (MCF10AT and MCF10AT3B) expressed the hpa gene (lanes 5 and 6) in correlation with their metastatic potential. The highly metastatic MCF10AT3B cells were derived from the third generation of xenografted tumors (36). The heparanase activity expressed by these cell lines was in correlation with their metastatic behavior (FIG. 2b).

In subsequent experiments, sense and antisense deoxigenin labeled RNA probes (600 bp fragment of the hpa cDNA) were employed to screen archivial paraffin embedded human breast tissue for expression of the hpa gene transcripts by in situ hybridization.

As shown in FIGS. 3a–f, massive expression of the hpa gene was observed in invasive breast carcinoma (3a) and breast adenocarcinoma (3c). The hpa gene was already expressed by differentiated epithelial cells of pre-malignant fibrocystic breast (3b) and in breast carcinoma tissue surrounding the area of tumor necrosis where little or no staining was observed (3d). Unlike the malignant tissue, normal breast tissue failed to express the hpa transcript as revealed by the lack of staining in tissue derived from reduction mammoplasty, both by the antisense (3e) and sense (3f) hpa probes.

Altogether, these results demonstrate a preferential expression of the hpa gene malignant breast carcinoma cells, indicating a potential application in early diagnosis of the disease, particularly in view of the positive staining detected already in the fibrocystic stage.

Figure 4:
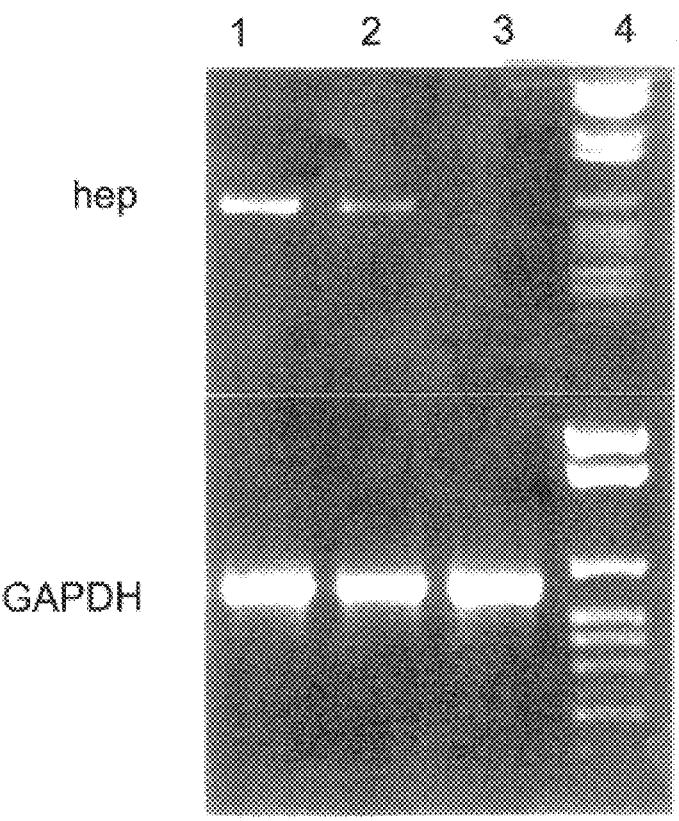
FIG. 4 demonstrate heparanase activity expressed by human prostate carcinoma cell lines. Expression of the human hpa gene by normal and malignant human prostate cells. Total RNA was isolated and subjected to RT-PCR using the appropriate human hpa primers (hep) and primers for the GAPDH housekeeping gene. Reactions without reverse transcriptase demonstrated no genomic DNA contamination in the RNA samples (not shown). Lane 1, metastatic DU145 human prostate carcinoma cells, lane 2, metastatic PC3 human prostate carcinoma cells, lane 3, normal human prostate tissue (biopsy specimen), lane 4, DNA molecular weight marker VI (Boehringer Mannheim).
Figure 5:
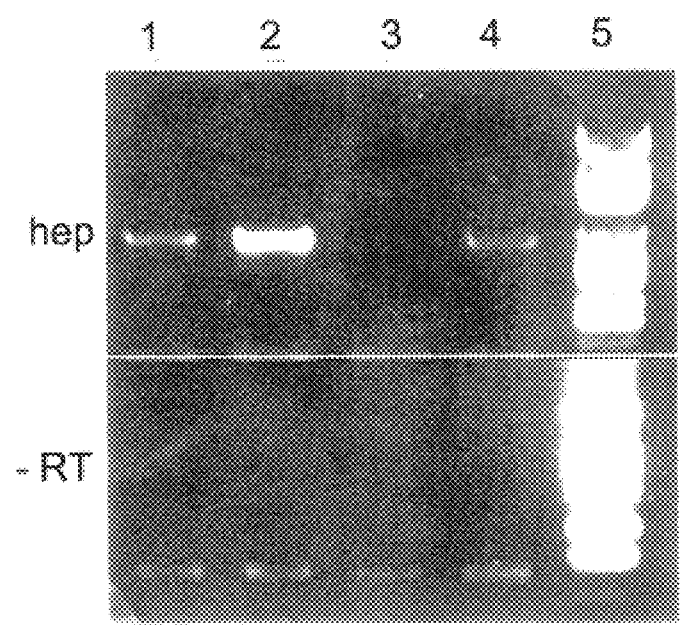
FIG. 5 demonstrate the expression of the hpa gene by high and low metastatic human bladder carcinoma and mouse T lymphoma cell lines. Total RNA was isolated and subjected to RT-PCR using human hpa primers. Lane 1, non metastatic MBT2 human bladder carcinoma cells, lane 2, highly metastatic T50 variant of MBT2 cells, lane 3, non-metastatic Eb mouse T-lymphoma, lane 4, highly metastatic ESb variant of the Eb mouse T-lymphoma cells, lane 5, DNA molecular weight marker VI (Boehringer Mannheim). –RT: negative control, without reverse transcriptase, P: non amplified primers.
Figure 6A:
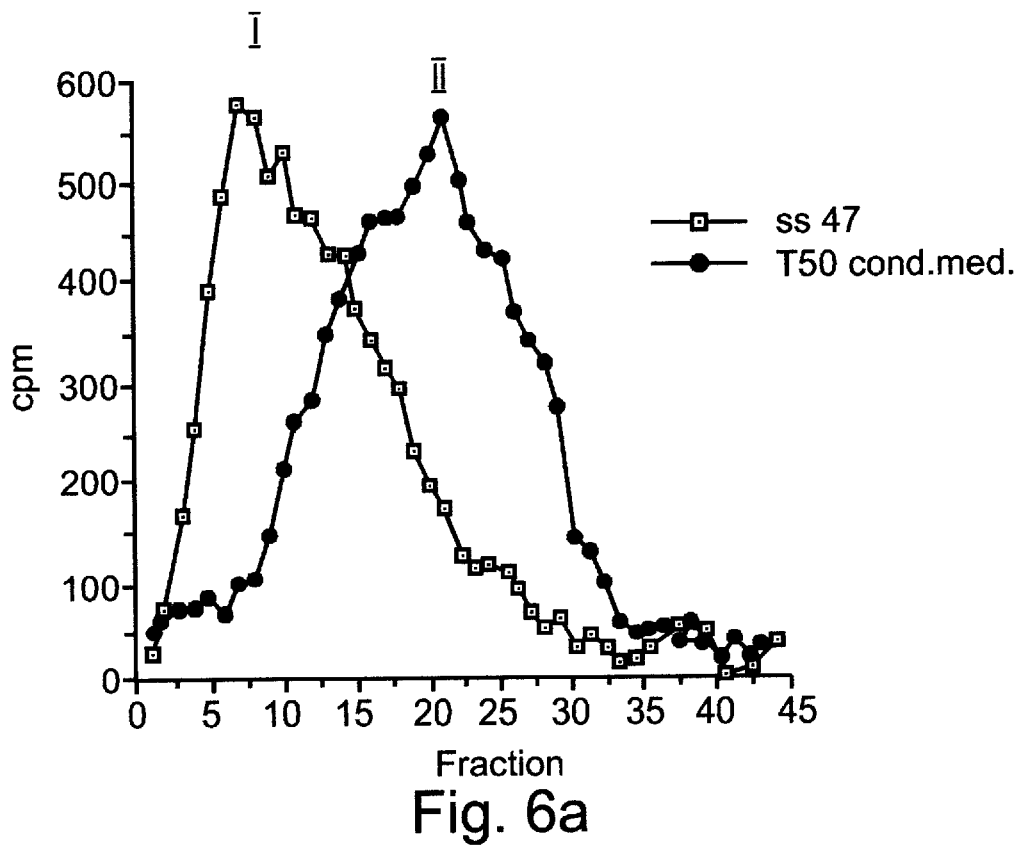
FIGS. 6a—c demonstrate heparanase activity expressed by high and low metastatic human bladder carcinoma cells. Media conditioned by low (MBT2) and high (T50) metastatic human bladder carcinoma cells were incubated (24 hours, 37° C., pH 6.2) with $^{35}$S-HSPG isolated from intact subendothelial ECM. Heparanase mediated conversion of the heparan sulfate substrate (peak I, ss 47) into low molecular weight degradation fragments (peak II) was analyzed by gel filtration on Sepharose 6B. Expression of the human hpa gene correlates with heparanase activity and metastasis in experimental animals.
Figure 6B:
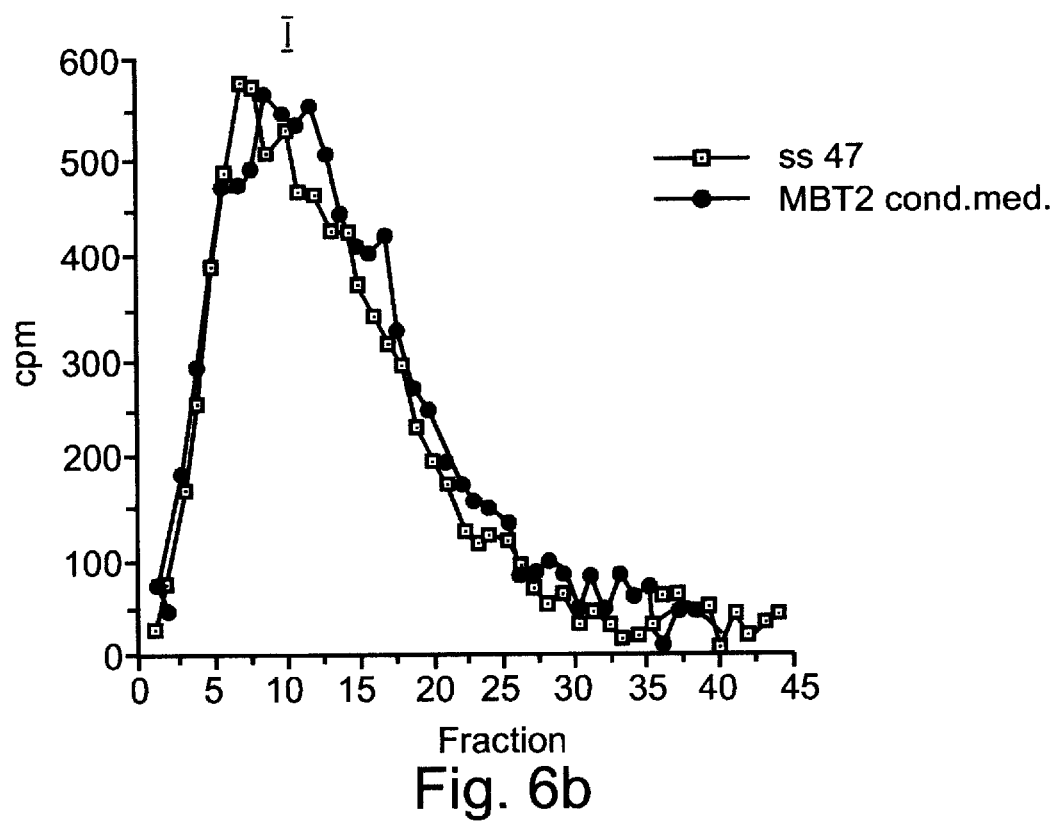
Figure 6C:
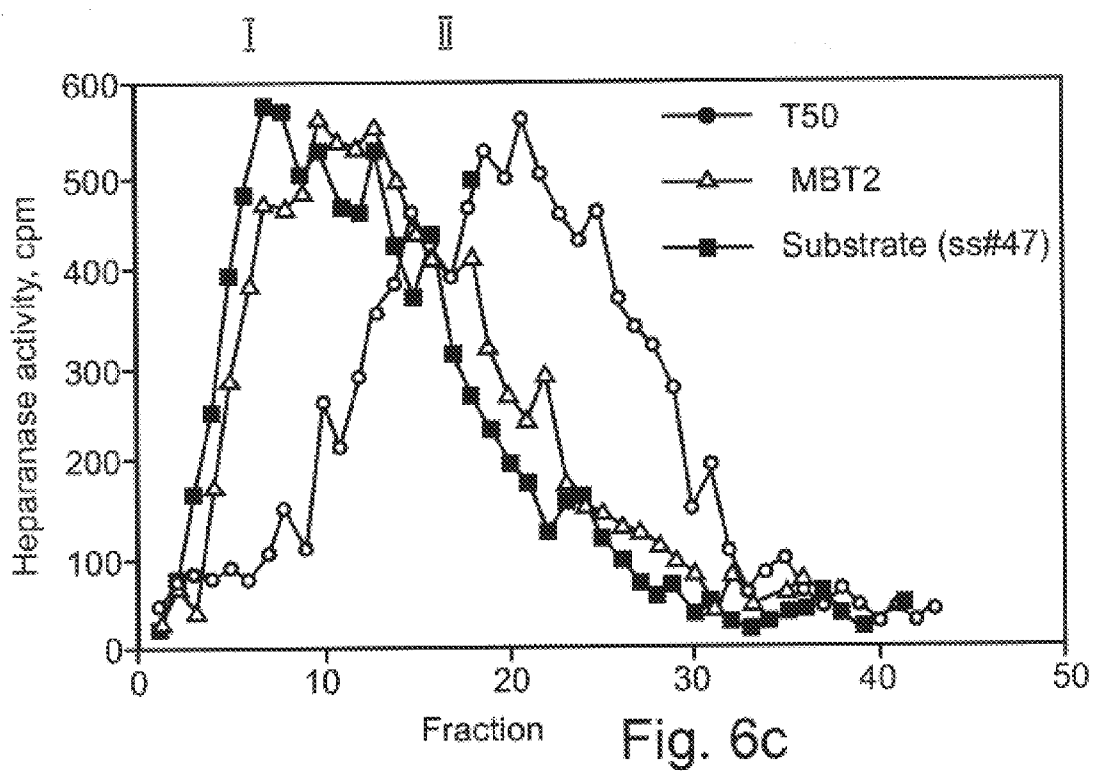

Human Prostate and Bladder Carcinomas:

Differential expression of the hpa mRNA was also suggested by RT-PCR analysis of several human prostate and bladder carcinoma cell lines. As demonstrated in FIG. 4, both DU145 (lane 1) and PC3 (lane 2) human prostate cell lines showed high expression of the hpa mRNA in contrast to lack of, or non-detectable, expression in a biopsy of normal adult prostate tissue (lane 3). Similarly, as demonstrated in FIG. 5, highly metastatic variant (T50) of the non-metastatic MBT2 human bladder carcinoma cell line, exhibited a much higher expression of the hpa gene (lane 2) as compared with the MBT2 cell line (lane 1). This difference was also reflected by high heparanase activity secreted into the culture medium of the aggressive T50 cells, as compared to no detectable activity in the medium of the parental MBT2 cells (FIGS. 6a–c). Again, the observed differential expression of the hpa gene and enzyme activity points toward potential application in the diagnosis of metastatic human prostate and bladder carcinomas.

Figure 7:
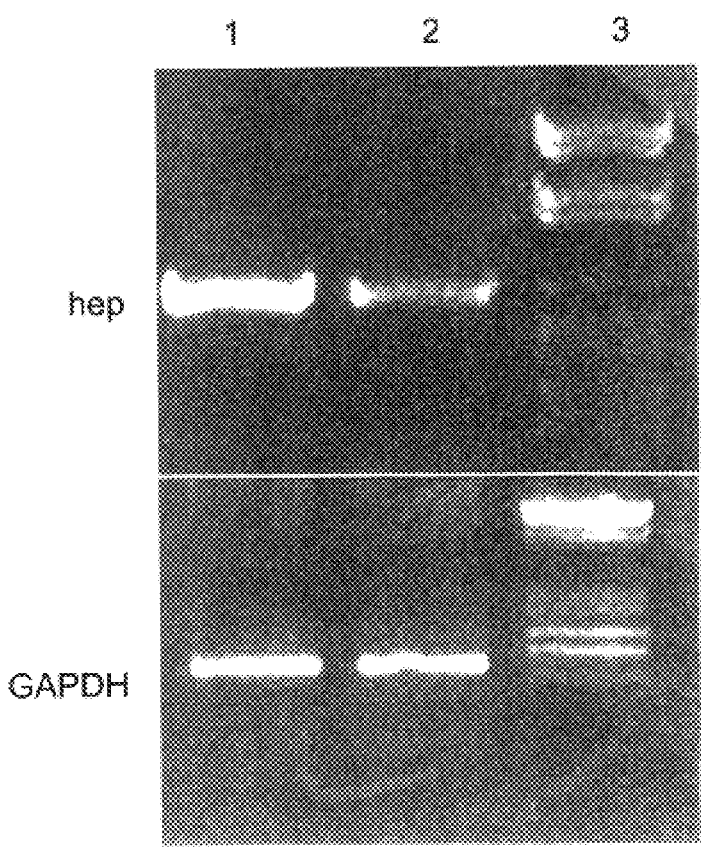
FIG. 7 demonstrate expression of the hpa gene by high and low metastatic B16 mouse melanoma cell lines. Total RNA was isolated and subjected to RT-PCR using hpa primers (hep) and primers for the GAPDH housekeeping gene. Reactions without reverse transcriptase demonstrated no genomic DNA contamination in the RNA samples. Lane 1, highly metastatic B16-F10 mouse melanoma cells, lane 2, low metastatic B16-F1 mouse melanoma cells, lane 3, DNA molecular weight marker VI (Boehringer Mannheim).

Mouse Melanoma and T-Lymphoma:

Differential expression of the hpa mRNA and heparan sulfate degrading activity, correlated with the metastatic potential in mice was also demonstrated in studies with mouse B16 melanoma and T-lymphoma. In fact, the melanoma (9, 37) and lymphoma (11) cell systems were the first experimental systems pointing toward an important role of heparanase in tumor cell invasion and metastasis. Our cloning of the hpa cDNA, encoding for the heparanase enzyme, provides, for the first time, an evidence that the difference in enzymatic activity is due primarily to a preferential expression of the hpa gene by highly metastatic tumor cells. Thus, as demonstrated in FIGS. 5 and 7, the highly metastatic ESb lymphoma (FIG. 5, lane 4) and B16-F10 melanoma (FIG. 7, lane 1) cell lines, expressed the hpa gene to a much higher extent as compared to the parental low metastatic Eb lymphoma (FIG. 5, lane 3) and B16-F1 melanoma (FIG. 7, lane 2) cells. The respective high and low levels of heparanase activity by these cell lines were reported in earlier studies (9, 11, 37).

Figure 8A:
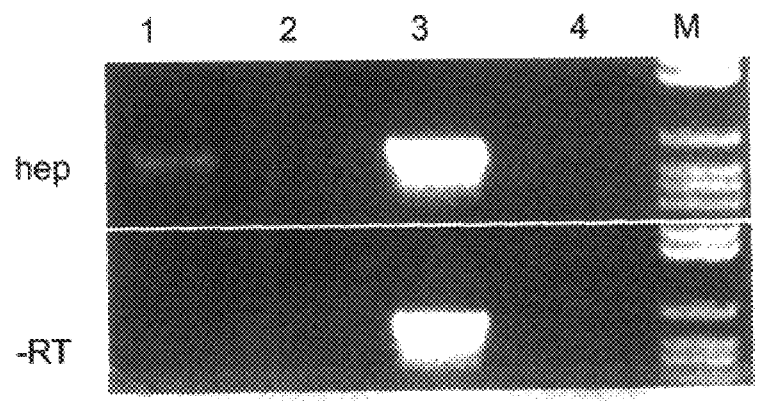
FIG. 8a demonstrate expression of the hpa gene by biopsy specimens from malignant human melanoma tumors and non-malignant benign nevus tissue which were processed for cell culture. Total RNA was isolated from subconfluent cultures and subjected to RT-PCR using human specific hpa primers (hep). Representative cases are shown. Lane 1, malignant melanoma, lane 2, non-malignant nevus tissue, lane 3, hpa-pcDNA plasmid (positive control), lane 4, negative control (no RNA), lane 5, DNA molecular weight marker VI (Boehringer Mannheim). Reactions without reverse transcriptase (–RT) demonstrated no genomic DNA contamination in the RNA samples.
Figure 8B:
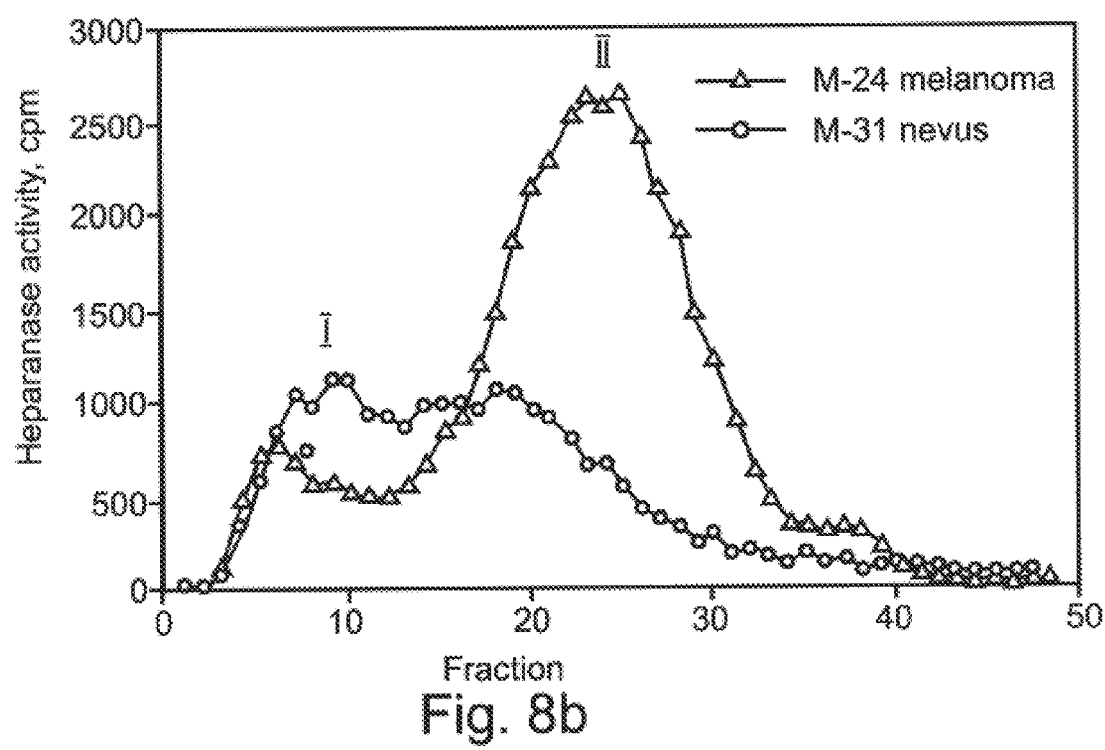
FIG. 8b demonstrates heparanase activity expressed by cultured cells derived from malignant melanoma (patient M-24) and non-malignant nevus tissue (patient M-31). Cultured cells were seeded on sulfate labeled ECM. Labeled degradation fragments released into the incubation medium were subjected to gel filtration on sepharose 6B.

Human Melanoma:

Preferential expression of the hpa gene and enzyme activity was also observed in cells derived from biopsies of human melanoma and normal nevus tissue. Biopsy specimens of malignant melanoma are routinely processed for cell culture in the department of Oncology (Hadassah Hospital, Jerusalem) for immunotherapy purposes. Cultured cells derived from 16 out of 16 patients (see also Table 1, below) expressed the hpa gene, as revealed by RT-PCR (FIG. 8a, lane 1, a representative patient). Melanoma cells derived from 3 of these patients were tested for degradation of soluble heparan sulfate proteoglycans and were found to be highly active (FIG. 8b). In contrast, cells derived from a non-malignant nevus tissue showed no detectable expression of the hpa mRNA (FIG. 8a, lane 2) and no enzyme activity (FIG. 8b).

Figure 9A:
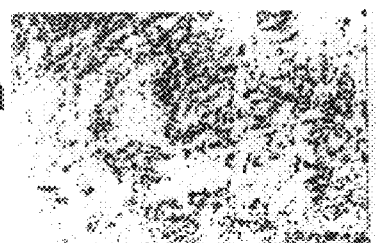
Figure 9B:
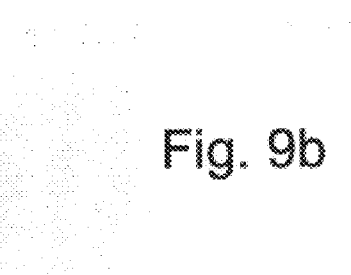

Similar results were obtained using archivial paraffin embedded biopsy specimens and in situ hybridization. Again, cytoplasmic labeling of the hpa mRNA was observed in tissue sections of metastatic specimens derived from 3 different patients with malignant melanoma (FIGS. 9a and 9c–d), but not from a non-malignant nevus (FIG. 9b). Altogether, these results imply a potential use of hpa specific primers, nucleic acid probes and antibodies in early diagnosis of melanoma metastasis.

Figure 10A:
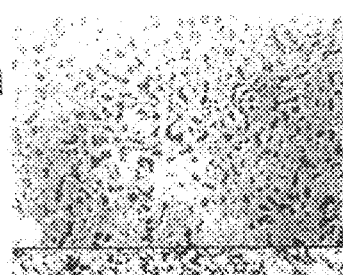
Figure 10B:
Figure 10C:
Figure 10E:
Figure 10F:

Human Liver Carcinoma:

The heparanase enzyme was first purified in our laboratory from a human hepatoma cell line (Sk-Hep-1). In fact, amino acid sequences derived from the purified hepatoma heparanase were used to clone the hpa gene. In situ hybridization studies revealed an intense expression of the hpa gene in tissue sections derived from human heaptocellular carcinoma (FIGS. 10a–b) and liver adenocarcinoma (FIG. 10c). The hpa mRNA was not expressed by adult normal liver tissue (FIG. 10d). It was expressed, however, in embryonic human liver (FIG. 10e). Each of these examples clearly supports the use of heparanase specific molecular probes as tools for early diagnosis of human cancer and its spread and response to anti-cancer treatments.

Other Human Tumors:

A preferential expression of the hpa gene was clearly observed by in situ hybridization performed with biopsy specimens of several different human carcinomas in comparison with their normal tissue counterparts. As demonstrated in FIGS. 11a–f, an intense expression of the hpa gene was observed in tissue sections derived from adenocarcinoma of the ovary (FIG. 11a), squameous cell carcinoma of the cervix (FIG. 11c), and colon adenocarcinoma (FIG. 11e). In contrast, there was little or no expression of the hpa mRNA in human tissue sections derived from normal ovary (FIG. 11b), cervix (FIG. 11d) and small intestine (FIG. 11f). The few cells stained in the normal tissue specimens were single infiltrating macrophages and neutrophils.

Positive staining of the hpa gene was also clearly seen in adenocarcinoma of the stomach (FIG. 12a), teratocarcinoma (FIG. 12b), well differentiated endometrial adenocarcinoma (FIG. 12c), adenocarcinoma of the pancreas (FIG. 12d), and mesothelioma (FIG. 12e). Each of these examples clearly supports the use of heparanase specific molecular probes as tools for early diagnosis of human cancer and its spread and response to anti-cancer treatments.

Figure 13A:
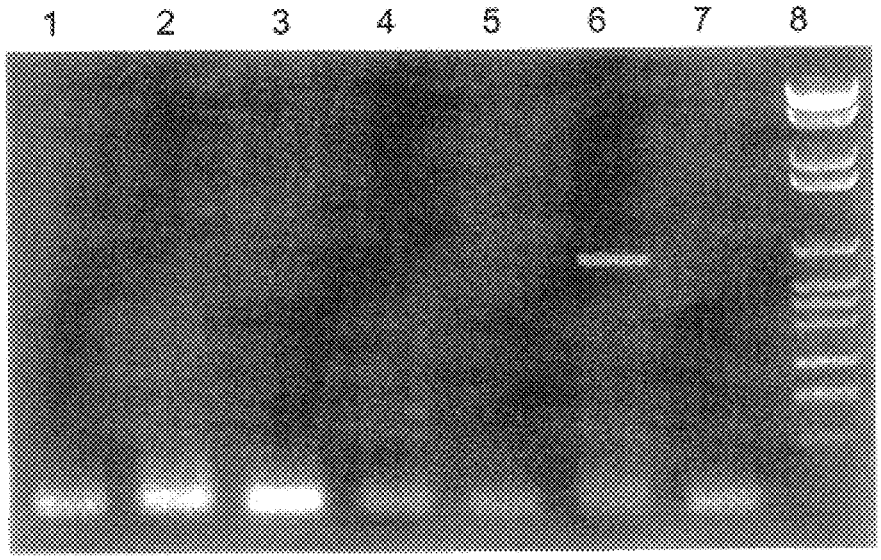
FIGS. 13a–b demonstrate expression of heparanase in human leukemias and lymphomas. Peripheral white blood cells of patients with various types of leukemia and lymphoma were isolated and tested for expression of the human hpa gene. For this purpose, total RNA was isolated and subjected to RT-PCR using human specific hpa primers. Reactions without reverse transcriptase demonstrated no genomic DNA contamination in the RNA samples. Peripheral white blood cells of different patients with chronic lymphocytic leukemia (FIG. 13a, lanes 1–5) were isolated and tested for expression of the human hpa gene. 13a Lane 6, hpa-pcDNA plasmid (positive control), lane 7, negative control (no reverse transcriptase), lane 8, DNA molecular weight marker VI (Boehringer Mannheim). Representative patients with various types of leukemia and lymphoma are shown in FIG. 13b. Lane 1, acute myelocytic leukemia, lane 2, Chronic lymphocytic leukemia (atypical B cell), lane 3, acute myelocytic leukemia (M5), lane 4, hairy cell leukemia, lane 5, non-hodjkin lymphoma (mature B cells), lane 6, non-hodjkin lymphoma (mature B cells), lane 7, chronic lymphocytic leukemia (stage I), lane 8, acute myelocytic leukemia (M2), lane 9, chronic myelocytic leukemia, lane 10, chronic lymphocytic leukemia (stage II), lane 11, acute lymphocytic leukemia, lane 12, chronic lymphocytic leukemia (stage III), lane 13, acute myelocytic leukemia (M1), lane 14, acute myelocytic leukemia (M3), lane 15, hpa-pcDNA plasmid (positive control), lane 16, negative control (no reverse transcriptase), lane 17, DNA molecular weight marker VI (Boehringer Mannheim).
Figure 13B:
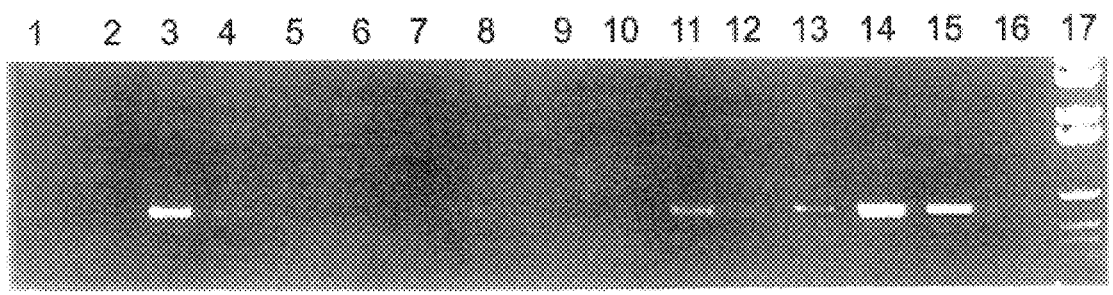
Figure 14:
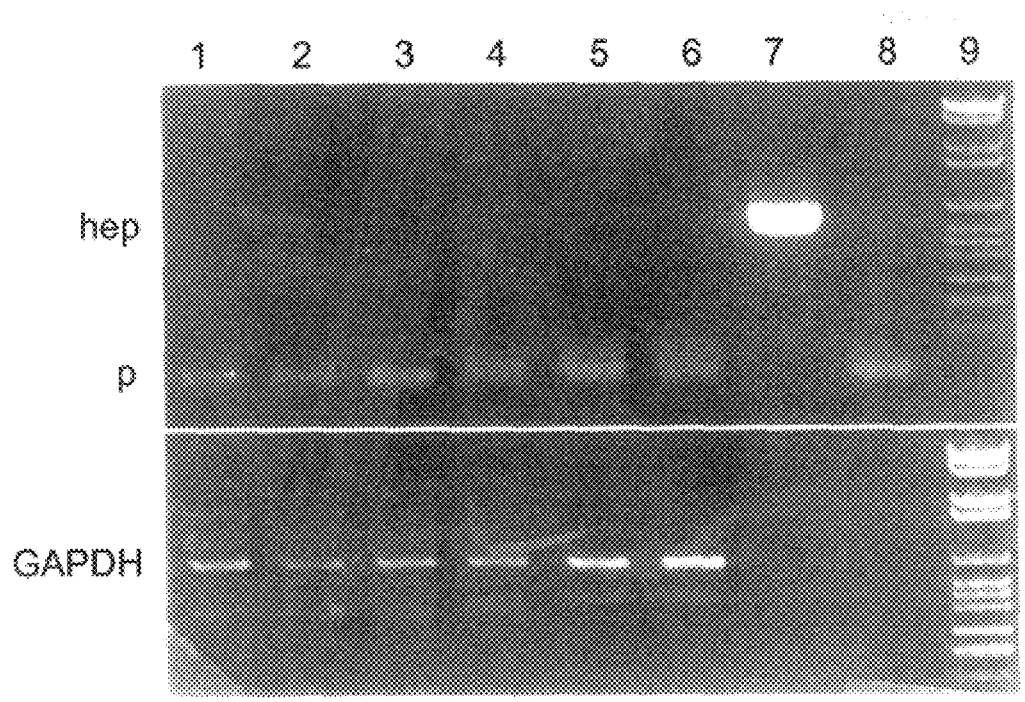
FIG. 14 demonstrates no expression of the hpa gene by normal human umbilical cord white blood cells. Total RNA was isolated and subjected to RT-PCR using hpa primers (hep) and primers for the GAPDH housekeeping gene. Reactions without reverse transcriptase demonstrated no genomic DNA contamination in the RNA samples. Lanes 1–6, white blood cell preparations from 6 different umbilical cords, lane 7, hpa-pcDNA plasmid (positive control), lane 8, negative control (no reverse transcriptase), lane 9, DNA molecular weight marker VI (Boehringer Mannheim).
Figure 15:
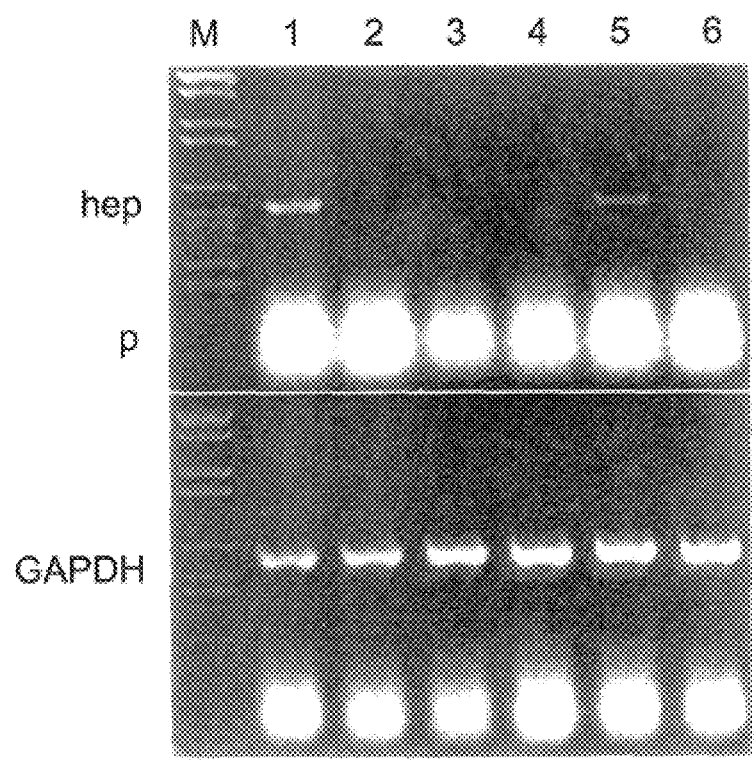
FIG. 15 demonstrates expression of the hpa gene by leukemia and lymphoma cell lines. Total RNA was isolated and subjected to RT-PCR using hpa primers (hep) and primers for the GAPDH housekeeping gene. Reactions without reverse transcriptase demonstrated no genomic DNA contamination in the RNA samples. Lane 1, normal B lymphoblastoid cell line (Monga), lane 2, Burkitt B lymphoma (Raji), lane 3, Burkitt B lymphoblasts (Daudi), lane 4, Burkitt B lymphoblasts (non Ebv, DG-75), lane 5, erythroleukemia (K-562), lane 6, pre B lymphoma (nalm$_6$), M=DNA molecular weight marker VI (Boehringer Mannheim).

Human Leukemia and Lymphoma:

We have previously applied time consuming measurements of heparanase activity and demonstrated that heparanase is expressed and readily secreted by acute and chronic human myeloid leukemic cells (AML and CML), but not by chronic lymphocytic leukemic cells (CLL). The availability of heparanase specific primers enables a more sensitive and rapid determination of hpa gene expression by human leukemia and lymphoma cells. For this purpose, peripheral white blood cells (derived from patients with leukemia and lymphoma) were purified on Ficoll-hypack and subjected to total RNA isolation and RT-PCR determination of the hpa mRNA. Altogether, cells of 69 patients were tested. Representative patients are presented in FIGS. 13a–b and the results are summarized in Table 1 below. Cells from 31 out of 31 patients with CLL showed no detectable expression of the hpa gene (FIG. 13a, lanes 1–5, FIG. 13b, lanes 2, 7, 10 and 12) regardless of the stage of the disease. Similar results were obtained with cells from 4 out of 4 patients with non-Hodjkin lymphoma (NHL) (FIG. 13b, lanes 5 and 6). Both the CLL and NHL cells represent primarily differentiated B cells. In contrast, the hpa mRNA was expressed by cells derived from 14 out of 14 patients with AML (FIG. 13b, lane 11). These cells represent undifferentiated myeloblasts of neutrophils and monocyte origin. The hpa mRNA was expressed in cells of 1 out of 3 patients with CML, and 2 out of 2 patients with acute lymphocytic leukemia. Surprisingly, umbilical cord blood derived white blood cells showed little (one case) or no expression (13 additional cases) of the hpa gene in different cord blood samples (FIG. 14, Table 1, below). These cord blood preparations are enriched with hematopoietic stem cells. Studies with established cell lines (FIG. 15) revealed no expression of the hpa mRNA in Burkitt B lymphoma (i.e., Raji, Daudi, DG-75, lanes 2–4, respectively), as opposed to mature normal B (Ebv transformed) lymphoblastoid cell line (i.e., monga, FIG. 15, lane 1) and erythroleukemia (K-562, lane 5).

Apparently, heparanase expression can distinguish between differentiated B cell lymphoma (CLL and NHL) and undifferentiated myelocytic and lymphoblastoid leukemia (AML and ALL) (Table 1). The lack of hpa gene expression by umbilical cord white blood cells may enable to distinguish between early normal white blood cells (hpa negative) and early leukemic cells (hpa positive). Furthermore, the presence of heparanase may distinguish between early lymphatic leukemic cells (hpa positive) and late B leukemia and lymphoma cells (hpa negative).

TABLE 1

Expression of hpa mRNA (RT-PCR) in human leukemia, lymphoma and melanoma

| Type | # of patients | # hpa positive | # hpa negative |
| --- | --- | --- | --- |
| CLL | 31 | 0 | 31 |
| AML | 14 | 14 | 0 |
| ALL | 2 | 2 | 0 |
| CML | 3 | 1 | 2 |
| NHL | 4 | 0 | 4 |
| Cord blood | 14 | 1 | 13 |
| Melanoma | 16 | 16 | 0 |
| Nevus (normal) | 3 | 0 | 3 |

Figure 16A:
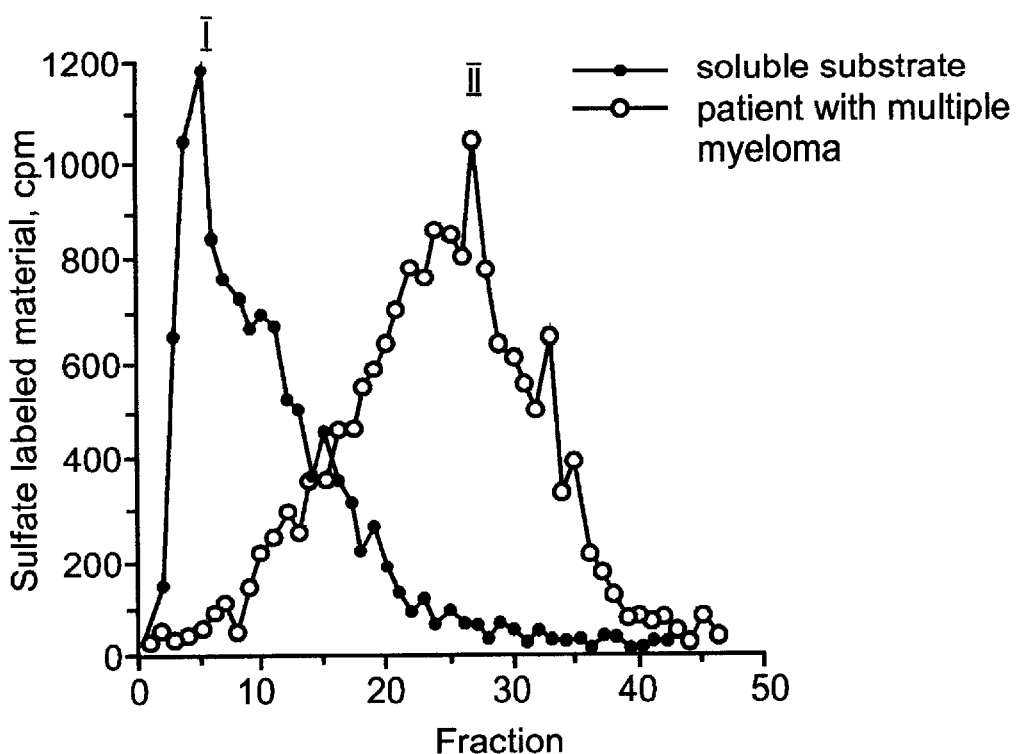
FIGS. 16a–h demonstrate urinary heparanase activity. Urine samples (o) of healthy donor (16d) and patients with multiple myeloma (16a), bilateral breast carcinoma (16b), metastatic breast carcinoma (16c), hemorrhagic nephritis (16e) nephrotic syndrome (16f), normoalbuminuric (16g) and microalbuminuric type I diabetes (16h) were incubated (24 hours, 37° C., pH 6.2) with $^{35}$S-HSPG (50 µl) isolated from intact subendothelial ECM (♦). Heparanase mediated conversion of the heparan sulfate substrate (peak I) into low molecular weight degradation fragments (peak II) was analyzed by gel filtration on Sepharose 6B.
Figure 16B:
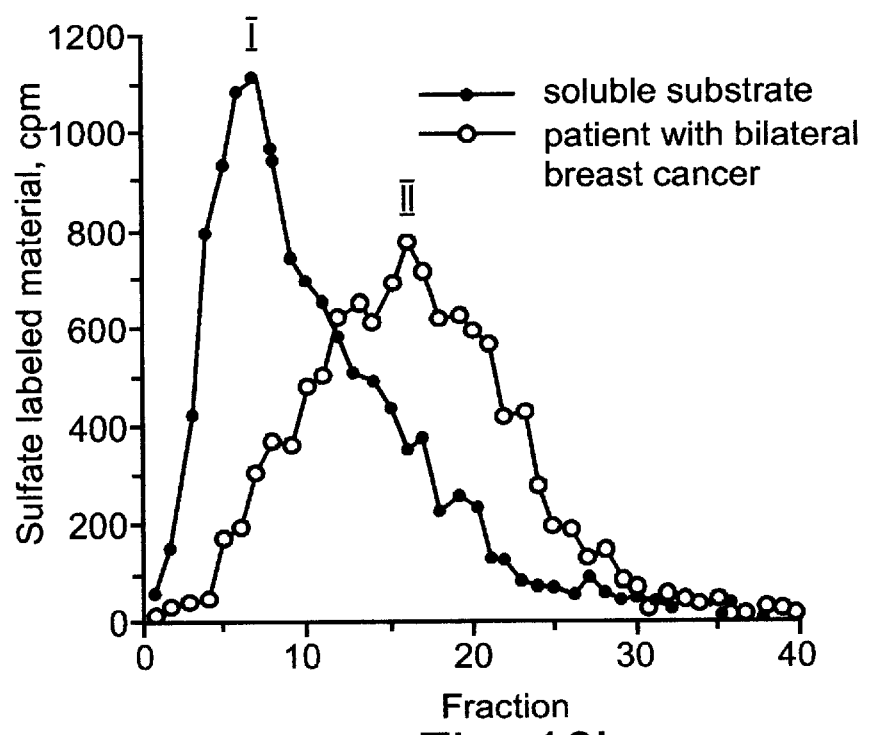
Figure 16C:
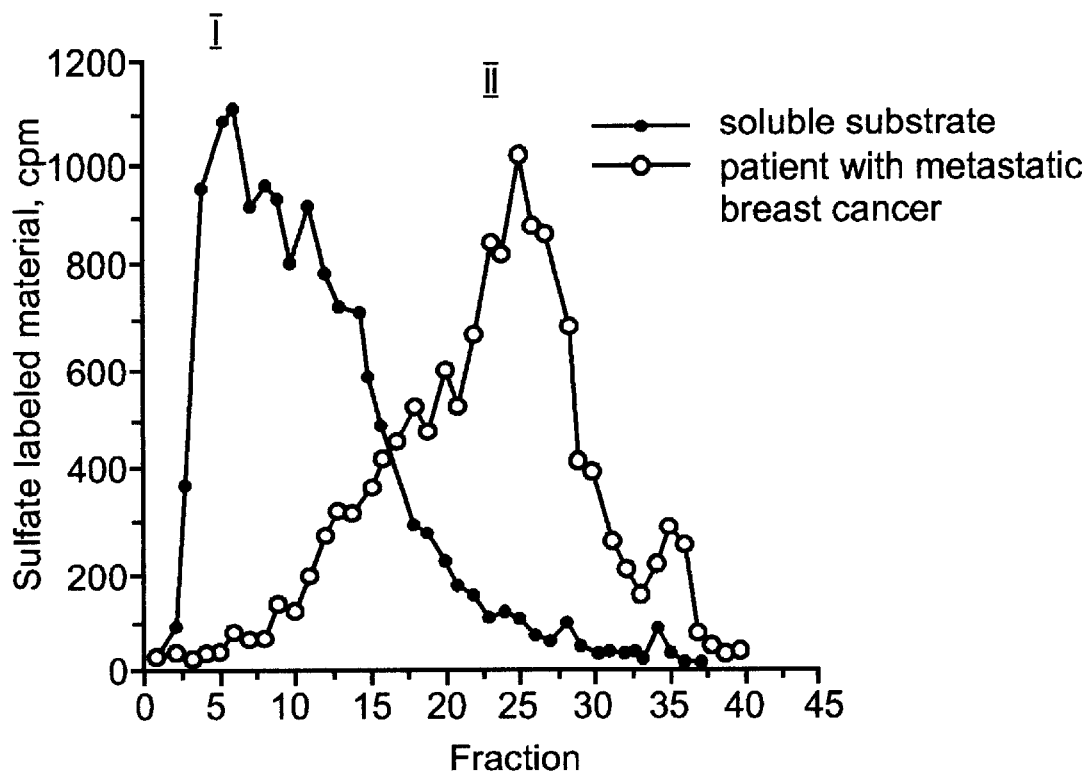
Figure 16D:
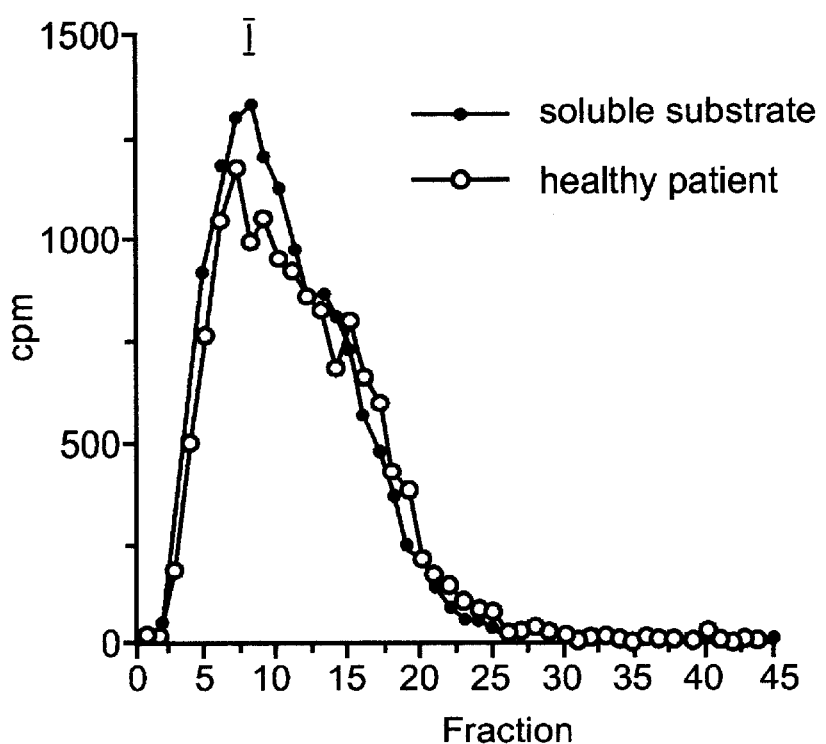

Heparanase Activity in the Urine of Cancer Patients:

In an attempt to elucidate the involvement of heparanase in tumor progression and its relevance to human cancer, we screened urine samples for heparanase activity. Heparanase activity was determined by incubation of urine with soluble sulfate labeled proteoglycans obtained by trypsin digestion of metabolically $Na_2^{35}SO_4$ labeled subendothelial extracellular matrix. Heparanase activity resulted in conversion of a high molecular weight (MW) sulfate labeled substrate into low MW heparan sulfate degradation fragments as determined by gel filtration analysis. Heparanase activity was detected in the urine of 21 (renal cell carcinoma, breast carcinoma, rabdomyosarcoma, stomach cancer, myeloma) out of 157 cancer patients. Three examples are given in FIGS. 16a–c. High levels of heparanase activity were determined in the urine of patients with an aggressive disease (primarily breast carcinoma, FIGS. 16b–c, multiple myeloma, FIG. 16a) and there was no detectable activity in the urine of healthy donors (FIG. 16d). A more sensitive ELISA is expected to detect the heparanase protein at early stages of the disease. Urine may also contain heparanase inhibitors (i.e., GAGs) and hence an activity assay may under estimate the number of patients with positive urinary heparanase protein.

Heparanase Activity in the Urine of Diabetic Patients:

Reduction in glomerular basement membrane (GBM) heparan sulfate proteoglycan (HSPG) is responsible for the microalbuminuria and proteinuria of diabetic nephropathy. We identified heparanase activity in cultured rat mesangial cells and postulated that the reduction in glomerular HSPG is secondary to increased glomerular heparanase activity and that the latter will be manifested by an increase in urinary heparanase. Urinary heparanase activity was tested in samples from 70 patients with type I diabetes and in 40 sex and age matched controls, as described above. The results are summarized in Table 2 below. Fifty patients were normoalbuminuric (NA) while 20 had microalbuminuria (MA). Urinary heparanase activity was detected in 13 of 70 (19%) diabetic patients while it was absent in the control group (p=0.002). Sixteen percent of the NA patients and 25% of the MA patients showed urinary heparanase activity (FIGS. 16g–h). Interestingly, over 80% of the heparanase positive patients were females. Heparanase positive patients had significantly higher blood glucose (p=0.0005) and HbA1C (p=0.03) levels compared with heparanase negative diabetic patients. This is the first study suggesting a role for heparanase in the pathogenesis of diabetic nephropathy. Urinary heparanase may be an early marker for renal involvement in type I diabetic patients, anteceding MA. The presence of heparanase activity in the urine of normo and microalbuminuric IDDM (insulin dependent diabetic mellitus) patients, is most likely due to diabetic nephropathy, the most important single disorder leading to renal failure in adults.

renal disease. The inability to discriminate the subpopulation that will develop renal damage prior to the appearance of microalbuminuria, 10–15 years following the diagnosis of diabetes, prevents us from significantly changing the devastating natural history of the disease. Urinary heparanase activity is a distinguishing feature, occurring in 30–35% of normoalbuminuric females, within an otherwise homogenous group of patients.

This is the first result suggesting a role for heparanase in the pathogenesis of proteinuria in type I diabetes. Obviously, measurements of urinary heparanase activity is both time consuming and not sensitive enough. Moreover, we have demonstrated the presence of an inhibitor of mammalian heparanase in the urine of normal individuals. The nature of this inhibitory substance, possibly urinary glycosaminoglycans is currently being studied. Urinary heparanase activity is therefore the result of a balance between the presence in the urine of the enzyme and its inhibitor(s). Immunodetection of the heparanase protein is therefore a more sensitive and straightforward approach for diagnostic purposes. Altogether, our results clearly indicate that anti-heparanase antibodies that identify the heparanase antigen can be applied for early diagnosis of cancer metastasis and renal

TABLE 2

Heparanase activity in urine of IDDM patients

| | No. of patients | Averaged Age | Sex | Disease duration | Blood pressure | GFR | Heparanase positive |
|---|---|---|---|---|---|---|---|
| Normo-albuminuria | 50 | 26.2 ± 8.5 years | 26 males 24 females | 16.5 ± 7.3 years | 112 ± 17 | 134 ± 25 ml/min/1.73 m$^2$ | 8/50 (16%) |
| Microalb-uminuria | 20 | 26.5 ± 11.2 years | 10 males 10 females | 14.5 ± 7.9 years | 115 ± 13 | 128 ± 26 ml/min/1.73 m$^2$ | 5/20 (25%) |

Repeated determination of urinary heparanase in 9 IDDM patients yielded similar results (6 negative and 3 positive) to the initial analysis performed 3 months earlier. Our results suggest that heparanase activity may play a role in the regulation of the number of HSPG anionic sites in the GBM and hence may modulate the permselective properties of the glomerular basement membrane.

Heparan sulfate contributes to the assembly and integrity of the ECM through binding to various ECM molecules such as collagen, laminin, fibronectin, thrombospondin and tenascin. Cleavage of heparan sulfate may therefore result in disassembly of the ECM leading to a loss of its barrier properties. We have identified heparanase activity expressed by mesanglial cells (not shown). Once heparanase is secreted by stimulated mesangial cells it will degrade heparan sulfate in the GBM thus allowing its passage into the urinary space.

Figure 16E:
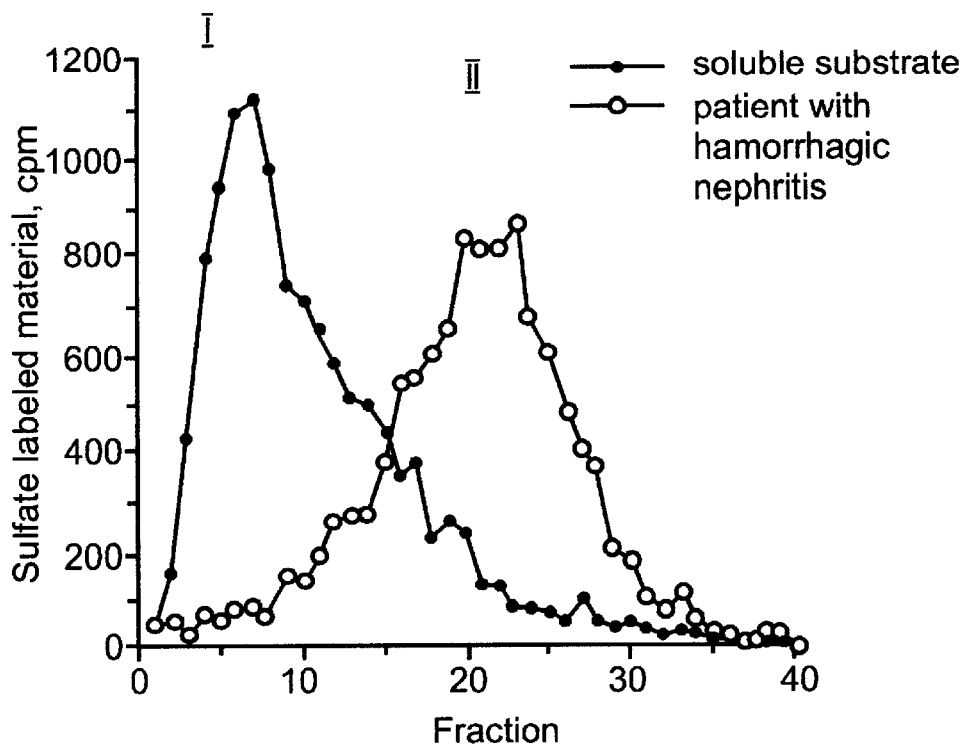
Figure 16F:
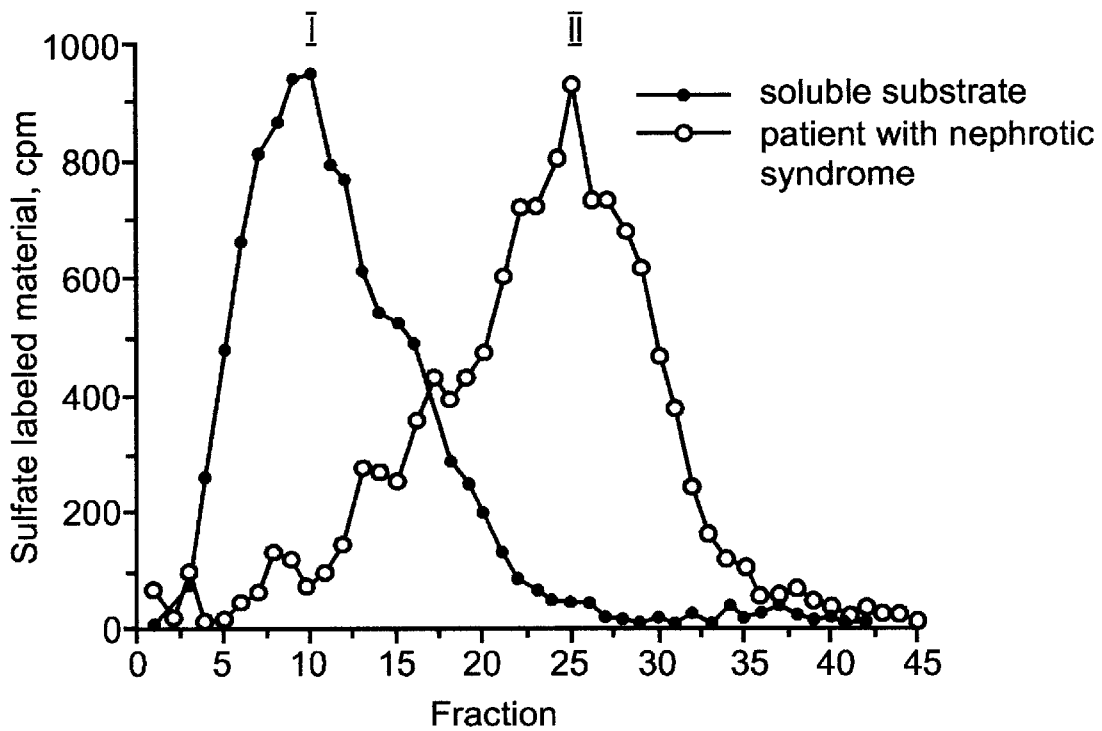
Figure 16G:
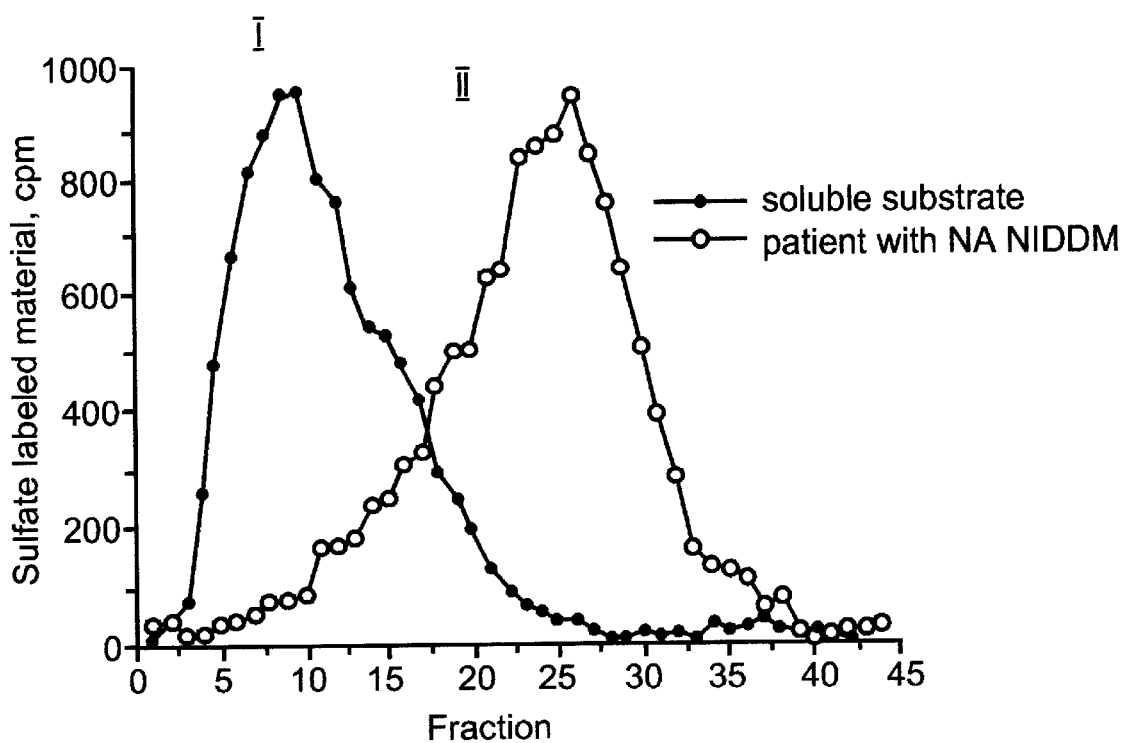
Figure 16H:
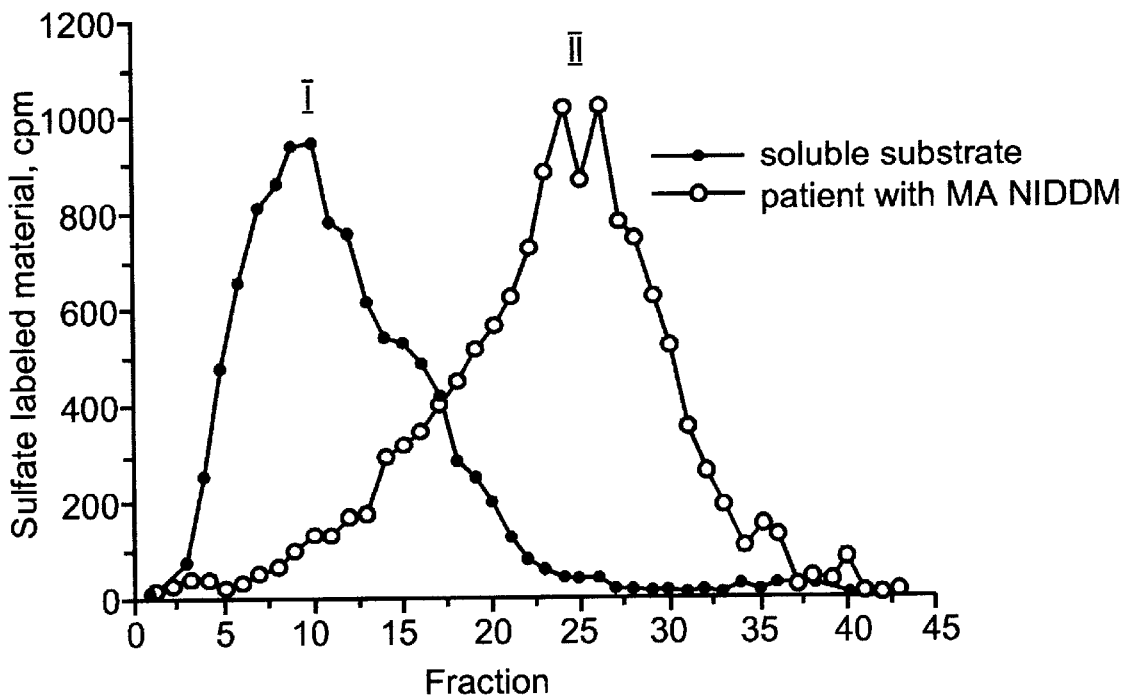

Heparanase activity was also detected in the urine of proteinuric patients not suffering from diabetes (FIGS. 16e–f). These included patients with focal segmental glomerulosclerosis, minimal change nephrotic syndrome and congenital nephrotic syndrome, thus indicating that the involvement of heparanase in the generation of proteinuria may not be limited to diabetic nephropathy. Urinary heparanase activity seems to be detected more frequently as the degree of proteinuria increases. Active heparanase was detected in the urine of 15% of normoalbuminuric and 25% microalbuminuric type I diabetic patients. The prevalence reached 48% in a group of 28 macroalbuminuric patients with NIDDM.

Diabetic nephropathy, occurring in approximately 30% of patients with type I diabetes, is a major cause of end stage diseases. As discussed above, it is conceivable that heparanase may overcome the filtration barrier of the glomerular basement membrane and ECM simply by virtue of its ability to degrade the HS moieties that are held responsible for their permeaselective properties. Urinary heparanase is therefore expected to reflect the presence of heparanase in the circulation and hence be a sensitive marker for metastatic, inflammatory and kidney disease. Of particular significance is the potential ability to follow the course of tumor progression and spread, response to anti-cancer treatments, and possible relapse of the disease in a given patient. Targeted drug delivery and therapy are another aspect of the use for such antibodies.

Figure 17A:
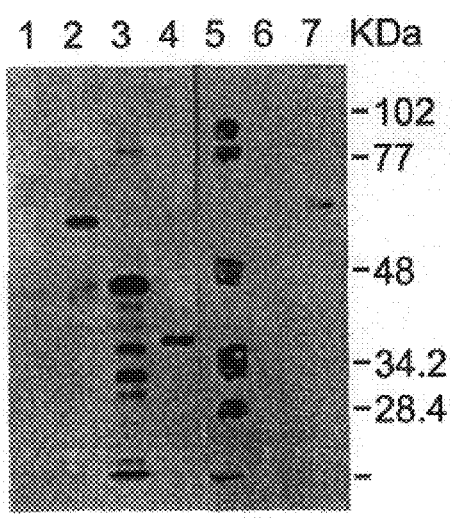
FIGS. 17a–b demonstrate Western blots of extracts of cells expressing various segments of heparanase as detected with polyclonal anti heparanase antibodies. 17a—antiserum from rabbit 7640, 17b—antiserum from rabbit 7644. Lane 1, E. coli BL21(DE3)pLysS cells transfected with pRSET, lane 2, E. coli BL21(DE3)pLysS cells transfected with pRSET containing the heparanase entire open reading frame (543 amino acids, SE ID NOs: 2 and 3), lane 3, E. coli BL21 (DE3)pLysS cells transfected with pRSEThpaBK containing 414 amino acids of the heparanase open reading frame (amino acids 130–543 of SEQ ID NOs: 2 and 3), lane 4, E. coli BL21(DE3)pLysS cells transfected with pRSEThpaBH containing 302 amino acids of the heparanase open reading frame (amino acids 130–431 of SEQ ID NOs: 2 and 3), lane 5, molecular size markers, lane 6, medium of Sf21 insect cells infected with recombinant Baculovirus pFhpa containing the heparanase entire open reading frame (543 amino acids, SEQ ID NOs: 2 and 3), lane 7, Sf21 insect cells infected with recombinant baculovirus with no insert. Proteins were separated on 10% SDS-PAGE, antisera were diluted 1:1,000. Detection was performed by ECL (Amersham) according to the manufacturer's instructions. Size in kDa is shown to the right, as was determined using prestained SDS-PAGE standards, Bio-Rad, CA.
Figure 17B:
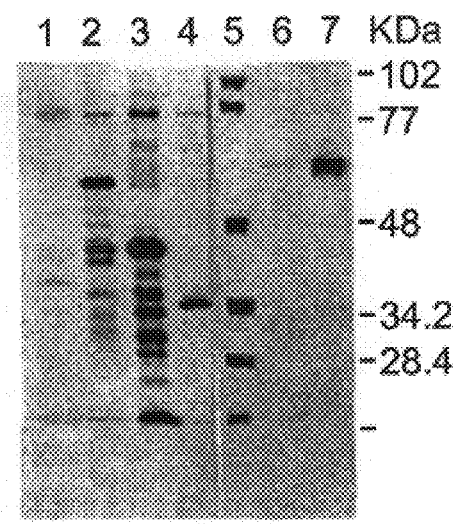

Anti-Heparanase Polyclonal Antibodies:

Antisera from two immunized rabbits were examined by western blot for reactivity with various segments of recombinant heparanase expressed in E. coli and with the Baculovirus expressed heparanase (FIGS. 17a–b). In both cases, the polyclonal antibody recognized proteins of the expected size in E. coli derived recombinant heparanase, about 60 kDa for the entire open reading frame (lanes 2), about 45 kDa for the 414 amino acids BamHI-KpnI hpa fragment (lanes 3) and 35 kDa for the 302 amino acids encoded by a BamHI-HindIII hpa fragment (lanes 4). A protein of approximately 65 kDa was recognized in the medium of Sf21 insect cells infected with recombinant Baculovirus pFhpa (lanes 7).

The specificity of affinity purified polyclonal antibodies was determined by Western blot with recombinant heparanase expressed in various expression systems, baculovirus infected insect cells, the yeast Pichia pastoris and CHO cells transfected with the hpa cDNA. For details about the CHO and Pichia clones see U.S. patent application Ser. No. 09/071,618, NOW ABANDONED, entitled "RECOMBINANT CELLS AND METHODS FOR EXPRESSING RECOMBINANT HEPARANASE AND METHOD OF PURIFYING SAME", filed on the date of filing of the present application, which is incorporated by reference as if fully set forth herein.

Figure 18:
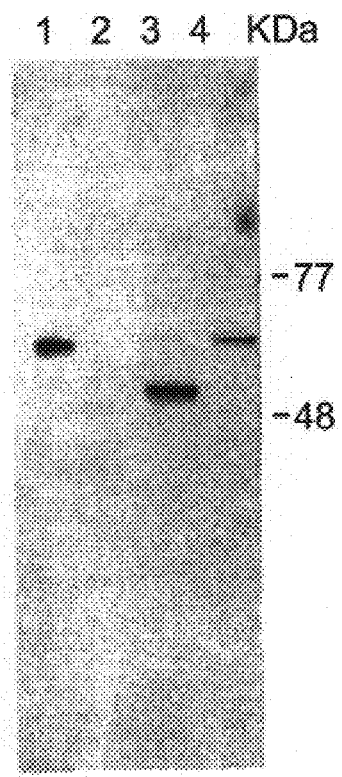
FIG. 18 demonstrates Western blot using affinity purified polyclonal antibodies with heparanase expressed in various expression systems. Lane 1. medium of Sf21 insect cells infected with recombinant Baculovirus pFhpa, lane 2, cell extract of a Chinese hamster ovary (CHO) clone stably transfected with a vector containing no insert, lane 3, cell extract of a CHO stable clone transfected with hpa eDNA, lane 4, proteins precipitated from medium of the yeast Pichia pastoris transfected with hpa cDNA. Proteins were separated on 4–20% gradient SDS-PAGE, antibody was diluted 1:100. Detection was performed by ECL (Amersham) according to the manufacturer's instructions. For CHO and Pichia clones see U.S. Pat, application Ser. No. 09/071,618, entitled "RECOMBINANT CELLS AND METHODS FOR EXPRESSING RECOMBINANT HEPARANASE AND METHOD OF PURIFYING SAME", filed on the date of filing of the present application, which is incorporated by reference as if fully set forth herein. Size in kDa is shown to the right, as was determined using prestained SDS-PAGE standards, Bio-Rad, CA.

The specificity of the purified antibody is demonstrated in FIG. 18. The purified antibody identified a single about 65 kDa protein expressed by *Pichia pastoris* (FIG. 18, lane 4), and a major band of similar size expressed by Sf21 cells infected with recombinant baculovirus (FIG. 18, lane 1). In a CHO stable transfected clone, 65 kDa and 50 kDa bands are detected (FIG. 18, lane 3) as compared with the negative control (FIG. 18, lane 2). In several experiments the two forms of the recombinant heparanase were identified, the higher form appeared as 60 to 65 kDa and the lower form as 45 to 50 kDa. Antibody 7644 was more specific and detected mainly the bands of the recombinant heparanase. 7460 detected several other cross reactive bands.

Figure 19A:
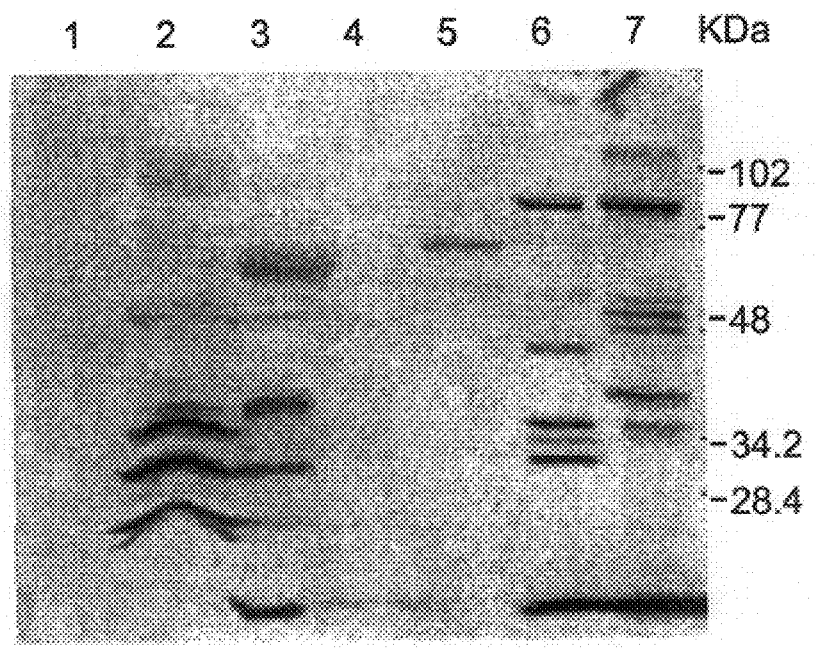
FIGS. 19a–b demonstrate Western blot of extracts of various cell types using anti-heparanase polyclonal antibodies. 19a—crude antiserum diluted 1:2,000, 19b—affinity purified antibodies diluted 1:100. lane 1, purified heparanase from placenta, lanes 2 and 3, cell extracts of platelets, insoluble and soluble fractions, respectively, lanes 4 and 5, cell extracts of neutrophils, insoluble and soluble fractions, respectively, lanes 6 and 7, cell extracts of mouse melanoma B16-F1 cells, insoluble and soluble fractions, respectively.
Figure 19B:
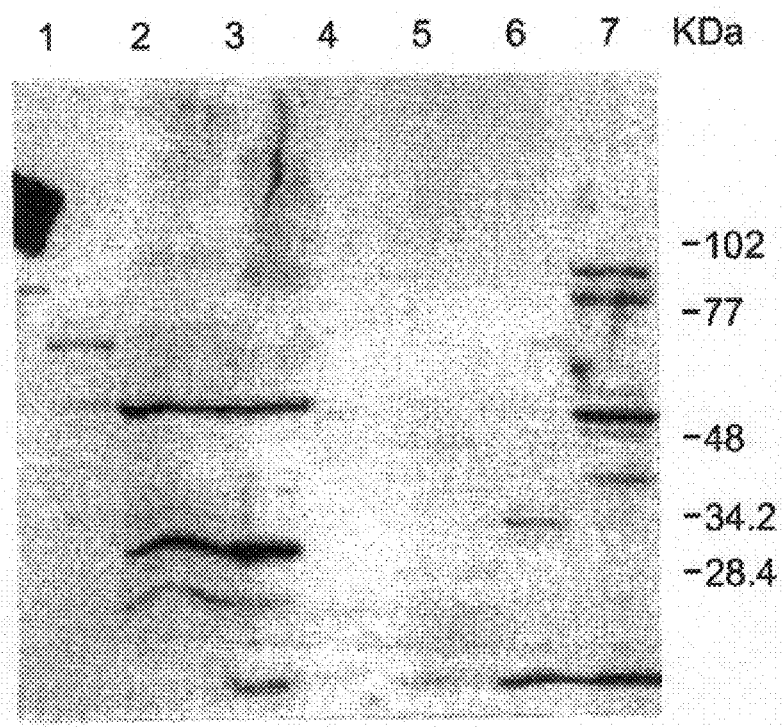

As shown in FIG. 19a, crude polyclonal antibodies recognized multiple bands in human platelets (lanes 2 and 3) and neutrophils cell extracts (lanes 4 and 5), as well as mouse melanoma cell line B 16 (lanes 6 and 7). However, as shown in FIG. 19b, affinity purified antibodies recognized the 65 kDa and 50 kDa forms of heparanase purified from placenta (lane 1), two major bands in platelets extract, an upper band of approximately 50 kDa which corresponds with the lower band of the purified protein and a lower band of about 30 kDa (lanes 2 and 3). The 50 kDa protein appears in mouse melanoma cells as well as two bands of a higher molecular weight and several minor bands, which represent cross reactive proteins or other species of heparanase (lanes 6 and 7).

Monoclonal Antibodies:

Eight hundred hybridomas, generated following 3 fusions were screened by ELISA for reactivity against human heparanase (native and denatured). Eight positive hybridomas were selected. Table 3 below summarizes the characteristics of the 8 hybridomas.

TABLE 3

Relative reactivity of hybridomas supernatants with native and denatured recombinant human heparanase

| Hybridoma | ELISA Native | ELISA Denature | Western blotting |
|---|---|---|---|
| HP-6 | − | + | n.d. |
| HP-40 | +++ | ++ | n.d. |
| HP-45 | + | ++ | n.d. |
| HP-92 | ++ | +++ | n.d/ |
| HP-117 | ++++ | +++ | 60, 45, 42 kDa |
| HP-130 | ++++ | +++ | n.d. |
| HP-239 | ++++ | +++ | n.d. |
| HP-303 | − | ++ | n.d. | n.d.-not determined

Immunoblot of native and recombinant heparanase expressed in various cell types was performed using the supernatant of hybridoma HP-117 (FIG. 20). A major band of approximately 50 kDa was detected in extract of stably transfected CHO cells (lane 3) and in platelets extract (lane 6). This band is also detected in transfected 293 cells as compared to the negative control (lanes 2 and 1 respectively). A band of approximately 42 kDa was observed in all mammalian cell extracts, including the negative control. This band probably represent a cross reactive protein or an endogenous form of heparanase. The 65 kDa recombinant heparanase purified from medium of baculovirus infected insect cells is clearly observed in lane 5 as well as a band of 53 kDa in lane 6 which is the expected size of the 508 amino acids heparanase polypeptide expressed in the *E. coli*. cells Both polyclonal and monoclonal antibodies were used successfully for detection of heparanase in intact cells by immunohistochemistry. Polyclonal antibodies showed specific staining of CHO cells transfected with pShpaCdhfr expression vector as described in patent U.S. patent application Ser. No. 09/071,618, now abandoned entitled "RECOMBINANT CELLS AND METHODS FOR EXPRESSING RECOMBINANT HEPARANASE AND METHOD OF PURIFYING SAME", filed on the date of filing of the present application, which is incorporated by reference as if. fully set forth herein, as compared with no staining of the non-transfected CHO cells (FIGS. 21a–b). Similar results were obtained with several monoclonal antibodies. FIGS. 22a–b demonstrate the specific staining of heparanase in the cytoplasm of transfected CHO cells, with supernatant of hybridoma HP-130. No staining was observed in non-transfected cells. Monoclonal antibody HP-92 showed a specific staining of neutrophils and platelets in blood smear of a healthy donor (FIGS. 23a–c). This expression pattern is consistent with the high levels of heparanase activity characteristic of these cells.

Availability of anti-heparanase antibodies will enable development of immunological assays for screening tissue and body fluids for heparanase. An ELISA will provide a more sensitive and convenient means of detection as compared to the currently available assays of heparanase activity which do not appear sensitive enough for the detection of the enzyme in non-concentrated plasma and body fluids.

ELISA will provide a powerful diagnostic tool for quantitative determination of heparanase concentrations in serum, plasma, urine and other biological fluids. Although platelets and activated cells of the immune system (11) can express heparanase activity under certain conditions, we have detected little or no heparanase activity in normal human plasma. The possibility arises that with cancer patients, particularly those with leukemia and lymphoma, heparanase is secreted into the blood stream. In fact, our studies indicate that both acute and chronic human myeloid leukemic cells (AML and CML), but not chronic lymphocytic leukemic cells (CLL), secrete substantial amounts of heparanase during short incubation in PBS at 4° C.

As described above, elevated levels of heparanase were detected in sera from metastatic tumor bearing animals and melanoma patients (13) and in tumor biopsies of cancer patients (15). High levels of heparanase activity were measured in the urine of patients with aggressive metastatic disease and there was no detectable activity in the urine of healthy donors.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

LIST OF REFERENCES CITED

1. Wight, T. N., Kinsella, M. G., and Qwamstromn, E. E. (1992). The role of proteoglycans in cell adhesion, migration and proliferation. Curr. Opin. Cell Biol. 4: 793–801.

2. Jackson, R. L., Busch, S. J., and Cardin, A. L. (1991). Glycosaminoglycans: Molecular properties, protein interactions and role in physiological processes. Physiol. Rev. 71: 481–539.
3. Wight, T. N. (1989). Cell biology of arterial proteoglycans. Arteriosclerosis 9:1-20.
4. Kjellen, L., and Lindahl, U. (1991). Proteoglycans: structures and interactions. Annu. Rev. Biochem. 60: 443–475.
5. Ruoslahti, E., and Yamaguchi, Y. (1991). Proteoglycans as modulators of growth factor activities. Cell 64: 867–869.
6. Vlodavsky, I., Bar-Shavit, R., Korner, G., and Fuks, Z. (1993). Extracellular matrix-bound growth factors, enzymes and plasma proteins. In Basement membranes: Cellular and molecular aspects (eds. D. H. Rohrbach and R. Timpl), pp 327–343. Academic press Inc., Orlando, Fla.
7. Vlodavsky, I., Eldor, A., Haimovitz-Friedman, A., Matzner, Y., Ishai-Michaeli, R., Levi, E., Bashkin, P., Lider, O., Naparstek, Y., Cohen, I. R., and Fuks, Z. (1992). Expression of heparanase by platelets and circulating cells of the immune system: Possible involvement in diapedesis and extravasation. Invasion & Metastasis 12: 112–127.
8. Vlodavsky, I., Mohsen, M., Lider, O., Ishai-Michaeli, R., Ekre, H. -P., Svahn, C. M., Vigoda, M., and Peretz, T. (1995). Inhibition of tumor metastasis by heparanase inhibiting species of heparin. Invasion & Metastasis 14: 290–302.
9. Nakajima, M., Irimura, T., and Nicolson, G. L. (1988). Heparanase and tumor metastasis. J. Cell. Biochem. 36: 157–167.
10. Liotta, L. A., Rao, C. N., and Barsky, S. H. (1983). Tumor invasion and the extracellular matrix. Lab. Invest. 49: 639–649.
11. Vlodavsky, I., Fuks, Z., Bar-Ner, M., Ariav, Y., and Schirrmacher, V. (1983). Lymphoma cell mediated degradation of sulfated proteoglycans in the subendothelial extracellular matrix: Relationship to tumor cell metastasis. Cancer Res. 43: 2704–2711.
12. Vlodavsky, I., Ishai-Michaeli, R., Bar-Ner, M., Fridman, R., Horowitz, A. T., Fuks, Z. and Biran, S. (1988). Involvement of heparanase in tumor metastasis and angiogenesis. Is. J. Med. 24: 464–470.
13. Parish, C. R., Coombe, D. R., Jakobsen, K. B., and Underwood, P. A. (1987). Evidence that sulphated polysaccharides inhibit tumor metastasis by blocking tumor cell-derived heparanase. Int. J. Cancer 40: 511–517.
14. Vlodavsky, I., Liu, G. M., and Gospodarowicz, D. (1980). Morphological appearance, growth behavior and migratory activity of human tumor cells maintained on extracellular matrix vs. plastic. Cell 19: 607–616.
15. Gospodarowicz, D., Delgado, D., and Vlodavsky, I. (1980). Permissive effect of the extracellular matrix on cell proliferation in-vitro. Proc. Natl. Acad. Sci. USA 77: 4094–4098.
16. Burgess, W. H., and Maciag, T. (1989). The heparin-binding (fibroblast) growth factor family of proteins. Annu. Rev. Biochem. 58: 575-606.
17. Folkman, J., and Klagsbrun, M. (1987). Angiogenic factors. Science 235: 442–447.
18. Vlodavsky, I., Bar-Shavit, R., Ishai-Michaeli, R., Bashkin, P., and Fuks, Z. (1991). Extracellular sequestration and release of fibroblast growth factor: a regulatory mechanism? Trends Biochem. Sci. 16: 268–271.
19. Cardon-Cardo, C., Vlodavsky, I., Haimovitz-Friedman, A., Hicklin, D., and Fuks, Z. (1990). Expression of basic fibroblast growth factor in normal human tissues. Lab. Invest. 63: 832–840.
20. Ishai-Michaeli, R., Eldor, A., and Vlodavsky, 1. (1990). Heparanase activity expressed by platelets, neutrophils and lymphoma cells releases active fibroblast growth factor from extracellular matrix. Cell Reg. 1: 833–842.
21. Campbell, K. H., Rennick, R. E., Kalevich, S. G., and Campbell, G. R. (1992) Exp. Cell Res. 200: 156–167.
22. Oosta, G. M., Favreau, L. V., Beeler, D. L., and Rosenberg, R. D. (1982) Purification and properties of human platelets heparitinase. J. Biol. Chem. 257: 11,249–11,255.
23. Hoogewerf, A. J., Leone, J. W., Reardon, M., Howe, W. J., Asa, D., Heinrikson, R. L., and Ledbetter, S. R. (1995). CXC chemokines connective tissue activating peptide-III and neutrophil activating peptide-2 are heparin/heparan sulfate-degrading enzymes. J. Biol. Chem. 270: 3268-3277.
24. Freeman, C., and Parish, C. R. (1988). Human platelet heparanase: Purification, characterization and catalytic activity. Biochem. J. 330:1341–1350.
25. Goshen, R., Hochberg, A., Korner, G., Levi, E., Ishai-Michaeli, R., Elkin, M., de Grot, N., and Vlodavsky, I. (1996) Purification and characterization of placental heparanase and its expression by cultured cytotrophoblasts. Mol. Human Reprod. 2: 679–684.
26. Jin, L., Nakajima, M. and Nicolson, G. L. (1990). Immunochemical localization of heparanase in mouse and human melanoma. Int. J. Cancer 45: 1088–1095.
26a. Mollinedo, F., Naagima, M., Leorens, A., Barbosa, e., Callejo, S., Gajate, C. and Fabras, a. (1997) Major co-localization of the extracellular-matrix degradative enzymes heparanase and gelatinase in tertiary granules of human neutrophils. Biochem. J. 327:917–923.
27. De Vouge, M. W., Yamazaki, A., Bennett, S. A. L., Chen, J. -H., Shwed, P. S., Couture, C., and Bimboim, H. C. (1994). Immuno selection of GRP94/endoplasmin from a KNRK cell specific λgt11 library using antibodies directed against a putative heparanase amino terminal peptide. Int. J. Cancer 56: 286–294.
28. Graham, L. D., and Underwood, P. A. (1996) Comparison of the heparanase enzyme from mouse melanoma cells, mouse macrophages and human platelets. Biochem. and Mol. Biol. International 39: 563–571.
29. Kosir, M. A., Quinn, C. C. V., Zukowski, K. L., Grignon, D. J., and Ledbetter, S. (1997) J. Surg. Res. 67: 98–105.
30. Kosir, M. A., Quinn, C. C. V., Pandey P., Berzinskas-Weller, E., Ledbetter, S. Fridman, R., and Wisscher, D. (1996) Cancer Res. 37: 495 (Ab. #3378).
30a. Ernst, S., Langer, R., Cooney, Ch. L., and Sasisekharan, R. (1995) Enzymatic degradation of glycosaminoglycans. Critical Reviews in Biochemistry and Molecular Biology: 30(5): 387–444.
31. Gospodarowicz, D., Mescher, A. L., Birdwell, C. R. (1977). Stimulation of corneal endothelial cell proliferation in vitro by fibroblast and epidermal growth factors. Exp Eye Res 25: 75–89.
32. Haimovitz-Friedman, A., Falcone, D. J., Eldor, A., Schirrmacher, V., Vlodavsky, I., and Fuks, Z. (1991). Activation of platelet heparitinase by tumor cell derived factors. Blood 78: 789–796.
33. Yelton, D. E., Scharff, M. D. (1981). Monoclonal antibodies: a powerful new tool in biology and medicine. Annu. Rev. Biochem. 50: 657-680.

34. Friedmann, Y. and Daniel, C. W. (1996). Regulated expression of homeobox genes Msx-1 and Msx-2 in the mouse mammary gland suggests a role in epithelial-stromal interactions, hormone action and neoplasia. Devel. Biol. 177: 347–355.
35. Soule, H. D., Maloney, T. M., Wolman, S. R., Peterson, W. D., et al. (1990) Cancer Res. 50: 6075–6086.
36. Mill, F. R., Soul, H. D., Tait, L., Pauley, R. J., Wolman, S. R., Dawson, P. J., and Heppner, G. H. (1993) J. Nat. Cancer Inst. 85: 1725-1732.
37. Nakajima, M., Irimura, T., DiFerrante, D., DiFerrante, N. and Nicolson, G. L. (1983) Heparan sulfate degradation: relation to tumor invasion and metastatic properties of mouse B16 melanoma sublines. Science 220: 611–613.

What is claimed is:

1. A method of detecting the presence, absence or level of a heparanase protein in a biological sample, the heparanase protein being specifically recognized by an anti-heparanase antibody, the anti-heparanase antibody being capable of binding a polypeptide as set forth in SEQ ID NO:2, the method comprising:

(a) extracting proteins from the biological sample, thereby obtaining a plurality of proteins;

(b) size separating said proteins;

(c) interacting said size separated proteins with the anti-heparanase antibody being capable of binding the polypeptide as set forth in SEQ ID NO:2; and (d) detecting the presence, absence or level of said interacted anti-heparanase antibody, thereby detecting the presence, absence or level of the heparanase protein in the biological sample.

2. The method of claim 1, wherein said anti-heparanase antibody is selected from the group consisting of a polyclonal antibody and a monoclonal antibody.

3. The method of claim 1, wherein said size separation is effected by electrophoresis.

4. A method of detecting the presence, absence or level of a heparanase protein in a biological sample, the heparanase protein being specifically recognized by an anti-heparanase antibody, the anti-heparanase antibody being capable of binding a polypeptide as set forth in SEQ ID NO:2, the method comprising:

(a) interacting the biological sample with the anti-heparanase antibody being capable of binding the polypeptide as set forth in SEQ ID NO:2; and (b) detecting the presence, absence or level of said anti-heparanase antibody specifically bound to at least a portion of said biological sample, thereby detecting the presence, absence or level of the heparanase protein in the biological sample.

5. The method of claim 4, wherein said biological sample is selected from the group consisting of a body fluid and a body tissue.

6. A method of detecting the presence, absence or level of a heparanase protein having an amino acid sequence as set forth in SEQ ID NO:2 in a biological sample, the heparanase protein being specifically recognized by an anti-heparanase antibody, the anti-heparanase antibody being capable of binding a polypeptide as set forth in SEQ ID NO:2, the method comprising reacting the biological sample with the anti-heparanase antibody being capable of binding the polypeptide as set forth in SEQ ID NO:2, and detecting the presence, absence or level of the anti-heparanase antibody, specifically bound to the heparanase protein, thereby detecting the presence, absence or level of the heparanase protein in the biological sample.

* * * * *